United States Patent
Shirazian et al.

(10) Patent No.: US 12,322,089 B2
(45) Date of Patent: Jun. 3, 2025

(54) PHYSICAL MEDICAL ELEMENT SIZING SYSTEMS AND METHODS

(71) Applicant: Intuitive Surgical Operations, Inc., Sunnyvale, CA (US)

(72) Inventors: Pourya Shirazian, Menlo Park, CA (US); Mahdi Azizian, San Jose, CA (US); Daniel Proksch, San Jose, CA (US); Azad Shademan, Campbell, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 468 days.

(21) Appl. No.: 17/639,676

(22) PCT Filed: Oct. 5, 2020

(86) PCT No.: PCT/US2020/054295
§ 371 (c)(1),
(2) Date: Mar. 2, 2022

(87) PCT Pub. No.: WO2021/071784
PCT Pub. Date: Apr. 15, 2021

(65) Prior Publication Data
US 2022/0292672 A1      Sep. 15, 2022

Related U.S. Application Data

(60) Provisional application No. 62/911,851, filed on Oct. 7, 2019.

(51) Int. Cl.
*G06T 7/00* (2017.01)
*A61B 34/20* (2016.01)
(Continued)

(52) U.S. Cl.
CPC ............ *G06T 7/0012* (2013.01); *A61B 34/20* (2016.02); *G06T 7/11* (2017.01); *G06T 19/006* (2013.01);
(Continued)

(58) Field of Classification Search
CPC ....... G06T 7/0012; G06T 7/11; G06T 19/006; G06T 19/20; G06T 2207/10081;
(Continued)

(56) References Cited

U.S. PATENT DOCUMENTS

| | | | | |
|---|---|---|---|---|
| 2004/0015070 A1* | 1/2004 | Liang | ..................... | G16H 50/20 600/407 |
| 2015/0024336 A1* | 1/2015 | Blassnig | ................ | H04N 23/56 433/29 |

(Continued)

FOREIGN PATENT DOCUMENTS

EP          2556804 A1      2/2013

OTHER PUBLICATIONS

International Preliminary Report on Patentability for Application No. PCT/US2020/054295, mailed Apr. 21, 2022, 9 pages.

(Continued)

*Primary Examiner* — Bo Joseph Peng

(57) ABSTRACT

An exemplary system is configured to instruct a display device to render a virtual medical element representative of a physical medical element over a target region within an image of an internal space of a patient, the target region depicting an anatomical surface to be covered by the physical medical element; receive, while the virtual medical element is rendered over the target region, user input that sets at least one of a pose of the virtual medical element within the image or a size of the virtual medical element; and determine, based on the user input and on depth data
(Continued)

representative of a depth map for the internal space, physical dimensions for the physical medical element.

20 Claims, 22 Drawing Sheets

(51) Int. Cl.
    *G06T 7/11*      (2017.01)
    *G06T 19/00*      (2011.01)
    *G06T 19/20*      (2011.01)

(52) U.S. Cl.
    CPC .... *G06T 19/20* (2013.01); *G06T 2207/10081* (2013.01); *G06T 2210/41* (2013.01); *G06T 2219/2012* (2013.01); *G06T 2219/2016* (2013.01); *G06T 2219/2021* (2013.01)

(58) Field of Classification Search
    CPC ......... G06T 2210/41; G06T 2219/2012; G06T 2219/2016; G06T 2219/2021; A61B 34/20; A61B 34/10; A61B 2034/104; A61B 2034/105; A61B 2034/107; A61F 2/0063
    See application file for complete search history.

(56) References Cited

U.S. PATENT DOCUMENTS

| | | | | |
|---|---|---|---|---|
| 2016/0191887 | A1* | 6/2016 | Casas | G02B 27/0172 348/47 |
| 2017/0007350 | A1* | 1/2017 | Popovic | A61B 34/10 |
| 2017/0124932 | A1* | 5/2017 | Evans, V | G06F 1/1637 |
| 2017/0372471 | A1* | 12/2017 | Eurèn | G06F 18/214 |
| 2018/0071032 | A1* | 3/2018 | de Almeida Barreto | G06T 19/006 |

OTHER PUBLICATIONS

International Search Report and Written Opinion for Application No. PCT/US2020/054295, mailed Mar. 4, 2021, 13 pages.
Invitation to Pay Additional Fees and International Search Authority for PCT/US2020/054295, mailed Jan. 11, 2021, 8 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

PHYSICAL MEDICAL ELEMENT SIZING SYSTEMS AND METHODS

RELATED APPLICATIONS

The present application is a U.S. National Stage Application under 35 U.S.C. § 371 of International Application No. PCT/US2020/054295, filed on Oct. 5, 2020, which claims priority to U.S. Provisional Patent Application No. 62/911,851, filed on Oct. 7, 2019, the contents of which are hereby incorporated by reference in their entirety.

BACKGROUND INFORMATION

A computer-assisted surgical system is often used to perform a hernia repair procedure within a patient. As part of the hernia repair procedure, a mesh patch may be placed over the hernia and attached (e.g., sutured) to tissue surrounding the hernia. The mesh patch may provide support for the damaged tissue as the tissue heals.

During a hernia repair procedure, a surgeon interacting with the computer-assisted surgical system must determine an appropriate size for the mesh patch. Once the mesh patch has been sized (e.g., by cutting the mesh patch out of a mesh material), the surgeon must place the mesh patch at an appropriate location within the patient. These and other types of operations that involve determining suitable physical dimensions for a medical element that is to be introduced into a patent may be time-intensive and tedious.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions and a processor communicatively coupled to the memory and configured to execute the instructions to instruct a display device to render a virtual medical element representative of a physical medical element over a target region within an image of an internal space of a patient, the target region depicting an anatomical surface to be covered by the physical medical element; receive, while the virtual medical element is rendered over the target region, user input that sets at least one of a pose of the virtual medical element within the image and a size of the virtual medical element; and determine, based on the user input and on depth data representative of a depth map for the internal space, physical dimensions for the physical medical element.

An exemplary system includes a memory storing instructions and a processor communicatively coupled to the memory and configured to execute the instructions to access image data representative of an image acquired by an imaging device and depicting an internal space of a patient; obtain depth data representative of a depth map for the internal space depicted in the image acquired by the imaging device; identify, based on the image data and the depth data, a target region within the image that depicts an anatomical surface to be covered by a physical medical element; and instruct a display device to render a virtual medical element representative of the physical medical element over the identified target region within the image.

An exemplary method includes instructing, by a medical element management system, a display device to render a virtual medical element representative of a physical medical element over a target region within an image of an internal space of a patient, the target region depicting an anatomical surface to be covered by the physical medical element; receiving, by the medical element management system while the virtual medical element is rendered over the target region, user input that sets at least one of a pose of the virtual medical element within the image and a size of the virtual medical element; and determining, by the medical element management system based on the user input and on depth data representative of a depth map for the internal space, physical dimensions for the physical medical element.

An exemplary method includes accessing, by a medical element management system, image data representative of an image acquired by an imaging device and depicting an internal space of a patient; obtaining, by the medical element management system, depth data representative of a depth map for the internal space depicted in the image acquired by the imaging device; identifying, by the medical element management system based on the image data and the depth data, a target region within the image that depicts an anatomical surface to be covered by a physical medical element; and instructing, by the medical element management system, a display device to render a virtual medical element representative of the physical medical element over the identified target region within the image.

An exemplary non-transitory computer-readable medium stores instructions that, when executed, direct a processor of a computing device to instruct a display device to render a virtual medical element representative of a physical medical element over a target region within an image of an internal space of a patient, the target region depicting an anatomical surface to be covered by the physical medical element; receive, while the virtual medical element is rendered over the target region, user input that sets at least one of a pose of the virtual medical element within the image and a size of the virtual medical element; and determine, based on the user input and on depth data representative of a depth map for the internal space, physical dimensions for the physical medical element.

An exemplary non-transitory computer-readable medium stores instructions that, when executed, direct a processor of a computing device to access image data representative of an image acquired by an imaging device and depicting an internal space of a patient; obtain depth data representative of a depth map for the internal space depicted in the image acquired by the imaging device; identify, based on the image data and the depth data, a target region within the image that depicts an anatomical surface to be covered by a physical medical element; and instruct a display device to render a virtual medical element representative of the physical medical element over the identified target region within the image.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
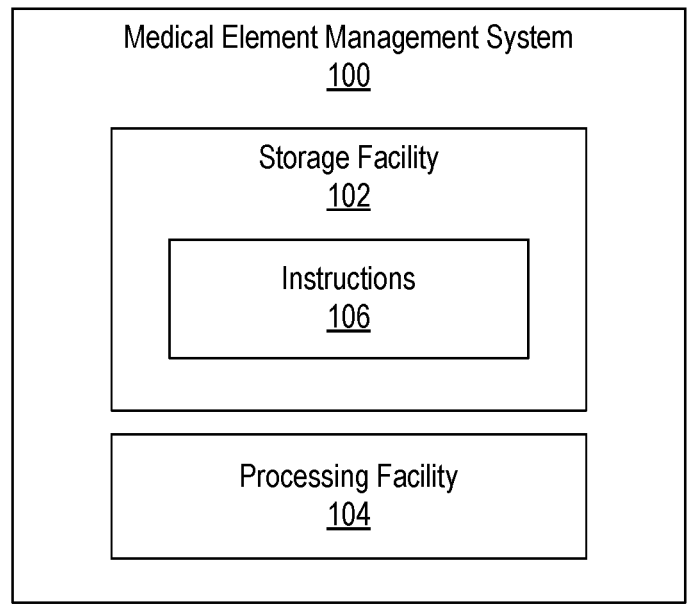
FIG. 1 illustrates an exemplary medical element management system according to principles described herein.

Physical medical element sizing systems and methods are described herein. As described herein, an exemplary medical element management system may instruct a display device to render a virtual medical element (e.g., a virtual mesh patch) representative of a physical medical element (e.g., a mesh patch for a hernia) over a target region within an image of an internal space of a patient, where the target region depicts an anatomical surface to be covered by the physical medical element. The medical element management system may receive, while the virtual medical element is rendered over the target region, user input that sets at least one of a pose of the virtual medical element within the image and a size of the virtual medical element. Based on the user input and on depth data representative of a depth map for the internal space, the medical element management system may determine physical dimensions for the physical medical element.

The systems and methods described herein advantageously facilitate optimal sizing of a physical medical element that is to be introduced into a body of a patient and placed over an anatomical surface within the body during a medical procedure. Moreover, by basing the determination of the physical dimensions for the physical medical element on depth data representative of a depth map for the internal space, the systems and methods described herein advantageously account for peaks, valleys, contours, and/or other variations in depth of the anatomical surface when determining the optimal size of the physical medical element. Such depth variations may not be visually apparent in an image of the internal space, and may affect the size of the physical medical element. For example, a large variation in depth between portions of the anatomical surface that is to be covered by the physical medical element may necessitate a larger size for the physical medical element than what may be visually ascertainable in the image of the internal space.

As an illustration, if a user manually adjusts a size of a virtual medical element displayed within an image that depicts an anatomical surface so that the virtual medical element appears to cover the anatomical surface, the size of the virtual medical element may not actually correspond to the actual size needed for the physical medical element unless depth data representative of the three-dimensional contours of the anatomical surface. Hence, the systems and methods described herein base the size of the anatomical surface on depth data that is indicative of such contours.

The systems and methods described herein may also advantageously determine where within an image of an internal space of a patient that the virtual medical element is to be initially rendered. This may facilitate relatively fast determination of an optimal size of the physical medical element represented by the virtual medical element, as will be described in more detail herein.

These and other advantages and benefits of the systems and methods described herein will be made apparent herein.

As used herein, a physical medical element refers to any element foreign to a patient's body that is configured to be placed on and cover an anatomical surface within the patient's body. For example, a physical medical element may be implemented by a patch (e.g., a mesh or wire patch) configured to cover a tissue defect (e.g., a hernia, cut, or other type of lesion) within the patient. Other examples of physical medical elements that may be used in connection with the systems and methods described herein include, but are not limited to, gauze, bandages, plates, prostheses (e.g., artificial discs, joint implants such as knee implants, etc.), specimen containment bags, bone putty, fasteners (e.g., clips, clamps, staples, etc.), etc. A physical medical element may be placed on an anatomical surface in any suitable manner. For example, the physical medical element may be sutured, anchored, or otherwise affixed to the anatomical surface.

FIG. 1 illustrates an exemplary medical element management system 100 ("system 100") configured to perform various operations described herein. As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). For example, facilities 102 and/or 104 may be implemented by any component in a computer-assisted surgical system configured to perform a medical procedure in which a physical medical element is introduced into a body of a patient and placed on an anatomical surface within the body of the patient. As another example, facilities 102 and/or 104 may be implemented by a computing device separate from and communicatively coupled to a computer-assisted surgical system. In some examples, facilities 102 and 104 may be distributed between multiple devices and/or multiple locations as may serve a particular implementation.

Storage facility 102 may maintain (e.g., store) executable data used by processing facility 104 to perform one or more of the operations described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations described herein.

For example, processing facility 104 may be configured to instruct a display device to render a virtual medical element representative of a physical medical element over a target region within an image of an internal space of a patient, the target region depicting an anatomical surface to be covered by the physical medical element, receive, while the virtual medical element is rendered over the target region, user input that sets at least one of a pose of the virtual medical element within the image and a size of the virtual medical element, and determine, based on the user input and on depth data representative of a depth map for the internal space, physical dimensions for the physical medical element. As described herein, the physical dimensions may define a surface area for the physical medical element.

As another example, processing facility 104 may be configured to access image data representative of an image acquired by an imaging device and depicting an internal space of a patient, obtain depth data representative of a depth map for the internal space depicted in the image acquired by the imaging device, identify, based on the image data and the depth data, a target region within the image that depicts an anatomical surface to be covered by a physical medical element, and instruct a display device to render a virtual medical element representative of the physical medical element over the identified target region within the image.

As another example, processing facility 104 may be configured to obtain anatomical characteristic data representative of a characteristic associated with an anatomical surface to be covered by a physical medical element, the anatomical surface within an internal space of a patient and determine, based on the anatomical characteristic data, a placement guidance parameter set. As described herein, the placement guidance parameter set may include one or more parameters configured to guide a placement of the physical medical element on the anatomical surface with one or more surgical instruments controlled by a computer-assisted surgical system.

As another example, processing facility 104 may be configured to obtain anatomical characteristic data representative of a characteristic associated with an anatomical surface to be covered by a physical medical element, the anatomical surface within an internal space of a patient, determine, based on the anatomical characteristic data, a suturing plan (or any other type of affixation plan) for suturing the physical medical element to the anatomical surface while the one or more surgical instruments controlled by the computer-assisted surgical system hold the physical medical element in place on the anatomical surface, and graphically indicate, within an image of the internal space, the suturing plan.

These and other operations that may be performed by system 100 (e.g., processing facility 104) are described herein.

Figure 2:
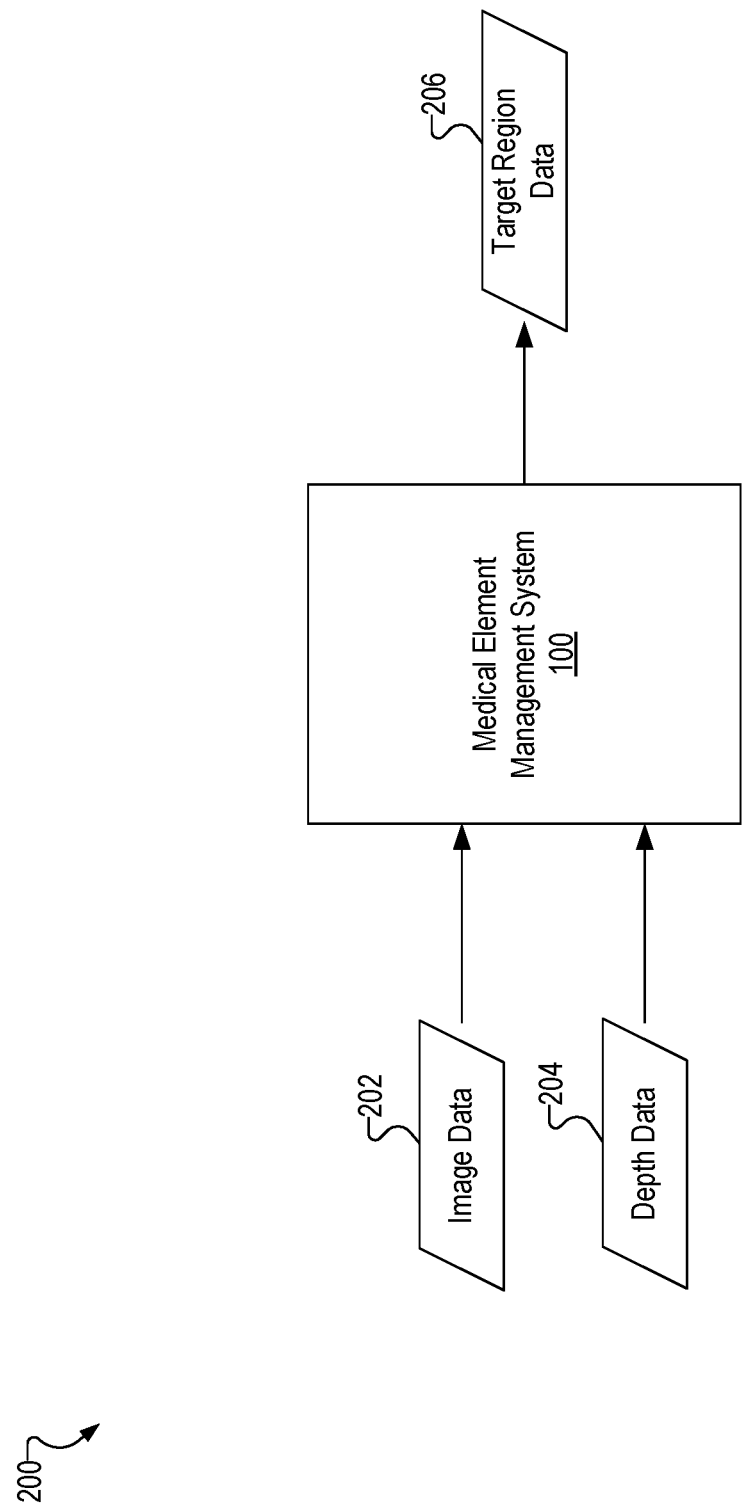
FIG. 2 illustrates an exemplary configuration in which a system is configured to identify a target region within an image acquired by an imaging device and that depicts an anatomical surface to be covered by a physical medical element according to principles described herein.

FIG. 2 illustrates an exemplary configuration 200 in which system 100 is configured to identify a target region within an image acquired by an imaging device and that depicts an anatomical surface to be covered by a physical medical element. As shown, system 100 may access image data 202 representative of an image acquired by an imaging device and depicting an internal space of a patient. System 100 may also obtain depth data 204 representative of a depth map for the internal space depicted in the image acquired by the imaging device. Based on image data 202 and depth data 204, system 100 may identify a target region within the image that depicts an anatomical surface to be covered by a physical medical element and output target region data 206 representative of the identified target region.

Target region data 202 may be in any suitable format. For example, target region data 202 may include two or three-dimensional pixel coordinates representative of pixels that depict the anatomical surface that is to be covered by the physical medical element.

Exemplary manners in which image data 202 and depth data 204 may be generated will now be described.

Figure 3:
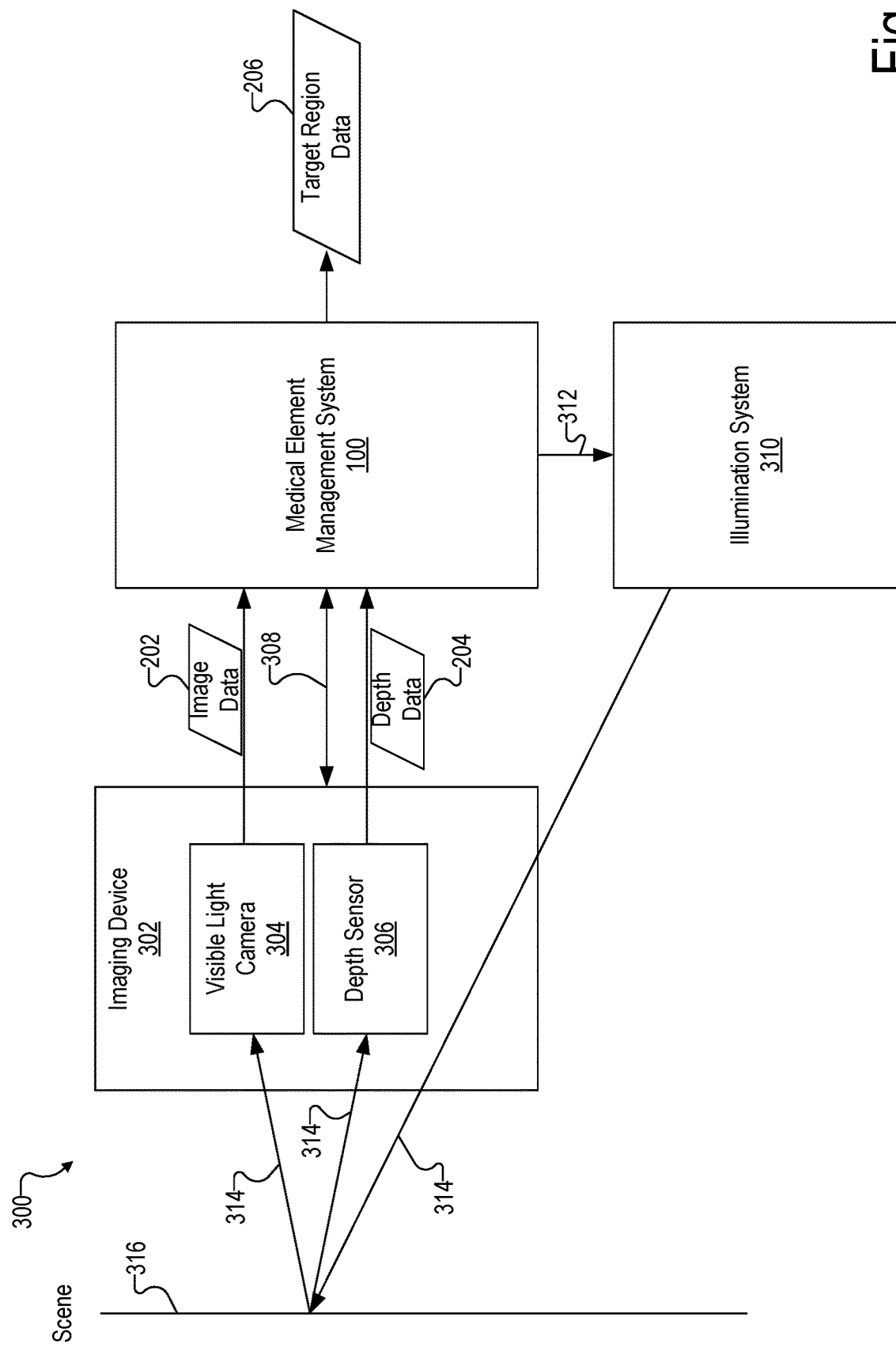
FIG. 3 illustrates an exemplary configuration in which an imaging device includes a visible light camera and a depth sensor according to principles described herein.

FIG. 3 illustrates an exemplary configuration 300 in which an imaging device 302 includes a visible light camera 304 configured to generate and output image data 202 and a depth sensor 306 configured to generate and output depth data 204.

Imaging device 302 may be implemented by an endoscope or other camera device configured to capture images of a scene. In some examples, imaging device 302 may be configured to be attached to and controlled by a computer-assisted surgical system. In alternative examples, imaging device 302 may be hand-held and operated manually by an operator (e.g., a surgeon).

In some examples, the scene captured by imaging device 302 may include a surgical area associated with a patient. The surgical area may, in certain examples, be entirely disposed within the patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments used to perform the surgical procedure are located. In certain example implementations, the surgical area entirely disposed within the patient may be referred to as an "internal space." As described herein, any internal anatomy of the patient (e.g., vessels, organs, and/or tissue) and/or surgical instruments located in the internal space may be referred to as objects and/or structures.

Visible light camera 304 ("camera 304") is configured to generate image data 202 representative of a two-dimensional visible light image of a scene. Camera 304 may be implemented by any suitable image sensor, such as a charge coupled device ("CCD") image sensor, a complementary metal-oxide semiconductor ("CMOS") image sensor, a hyperspectral camera, a multispectral camera, or the like.

Depth sensor 306 may be implemented by any suitable sensor configured to generate depth data 204. For example, depth sensor 306 may be implemented by a time-of-flight sensor, a structured light sensor, an interferometer, a hyperspectral camera, a multispectral camera, and/or any other suitable sensor configured to acquire depth data as may serve a particular implementation. In cases where depth sensor 306 is implemented by a time-of-flight sensor, the time-of-flight sensor may be implemented by one or more photodetectors (e.g., one or more single photon avalanche diode ("SPAD") detectors), CCD sensors, CMOS sensors, and/or any other suitable configuration. In the example of FIG. 3, depth sensor 306 is separate from (i.e., physically distinct from) camera 304.

In configuration 300, system 100 may obtain image data 202 by directing camera 304 to acquire image data 202 and receiving image data 202 from camera 304. Likewise, system 100 may obtain depth data 204 by directing depth sensor 306 to acquire depth data 204 and receiving depth data 204 from depth sensor 306.

To this end, in configuration 300, system 100 is communicatively coupled to imaging device 302 by way of a bidirectional communication link 308 and to an illumination system 310 by way of a communication link 312. Communication links 308 and 312 may each be implemented by any suitable wired and/or wireless communication medium as may serve a particular implementation. System 100 may use communication links 308 and 312 to direct camera 304 and depth sensor 306 to acquire image data 202 and depth data 204 and receive image data 202 and depth data 204, as described herein.

Illumination system 310 may be configured to emit light 314 (e.g., at the direction of system 100) used to illuminate a scene to be imaged by imaging device 302. The light 314 emitted by illumination system 310 may include visible light and/or non-visible light (e.g., infrared light). As shown, light 314 may travel to the scene through imaging device 302 (e.g., by way of an illumination channel within imaging device 302 that may be implemented by one or more optical fibers, light guides, lenses, etc.).

As shown, light 314 emitted by illumination system 310 may reflect off a surface 316 within a scene being imaged by imaging device 302. In cases where imaging device 302 is aimed at an internal space of the patient, surface 316 represents a surface (e.g., an anatomical surface) within the internal space.

Camera 304 and depth sensor 306 may each detect the reflected light 314. Camera 304 may be configured to generate, based on the detected light, image data 202 representative of a two-dimensional visible light image of the scene including surface 316. Depth sensor 306 may be configured to generate, based on the detected light, depth data 204. Image data 202 and depth data 204 may each have any suitable format.

To generate a stereoscopic image of a scene, system 100 may direct illumination system 310 to emit light 314. System 100 may also activate (e.g., turn on) visible light camera 304 and depth sensor 306. Light 314 travels to the scene and reflects off of surface 316 (and, in some examples, one or more other surfaces in the scene). Camera 304 and depth sensor 306 both detect the reflected light 314.

Camera 304 (and/or other circuitry included in imaging device 302) may generate, based on detected light 314, image data 202 representative of a two-dimensional visible light image of the scene. This may be performed in any suitable manner. Visible light camera 304 (and/or other circuitry included imaging device 302) may transmit image data 202 to system 100. This may also be performed in any suitable manner.

Depth sensor 306 may generate, based on detected light 314, depth data 204 representative of a depth map of the scene (e.g., a depth map of surface 316). This may be performed in any suitable manner. For example, depth sensor 306 may measure an amount of time that it takes for a photon of light 314 to travel from illumination system 310 to depth sensor 306. Based on this amount of time, depth sensor 306 may determine a depth of surface 316 relative to a position of depth sensor 306. Data representative of this depth may be represented in depth data 204 in any suitable manner. For example, the depth map represented by depth data 204 may include an array of depth values (e.g., Z-buffer values) corresponding to each pixel in an image.

Depth sensor 306 (and/or other circuitry included imaging device 302) may transmit depth data 204 to system 100. This may be performed in any suitable manner.

System 100 may receive image data 202 and depth data 204 and perform one or more processing operations on image data 202 and depth data 204. For example, as will be described in more detail below, system 100 may generate target region data 206 based on image data 202 and depth data 204.

As another example, system 100 may generate, based on image data 202 and depth data 204, a right-side perspective image of the scene and a left-side perspective image representative of the scene. This may be performed in any suitable manner. System 100 may then direct display devices to concurrently display the right and left-side perspective images in a manner that forms a stereoscopic image of the scene. In some examples, the display devices are included in and/or communicatively coupled to computer-assisted surgical system 204.

Figure 4:
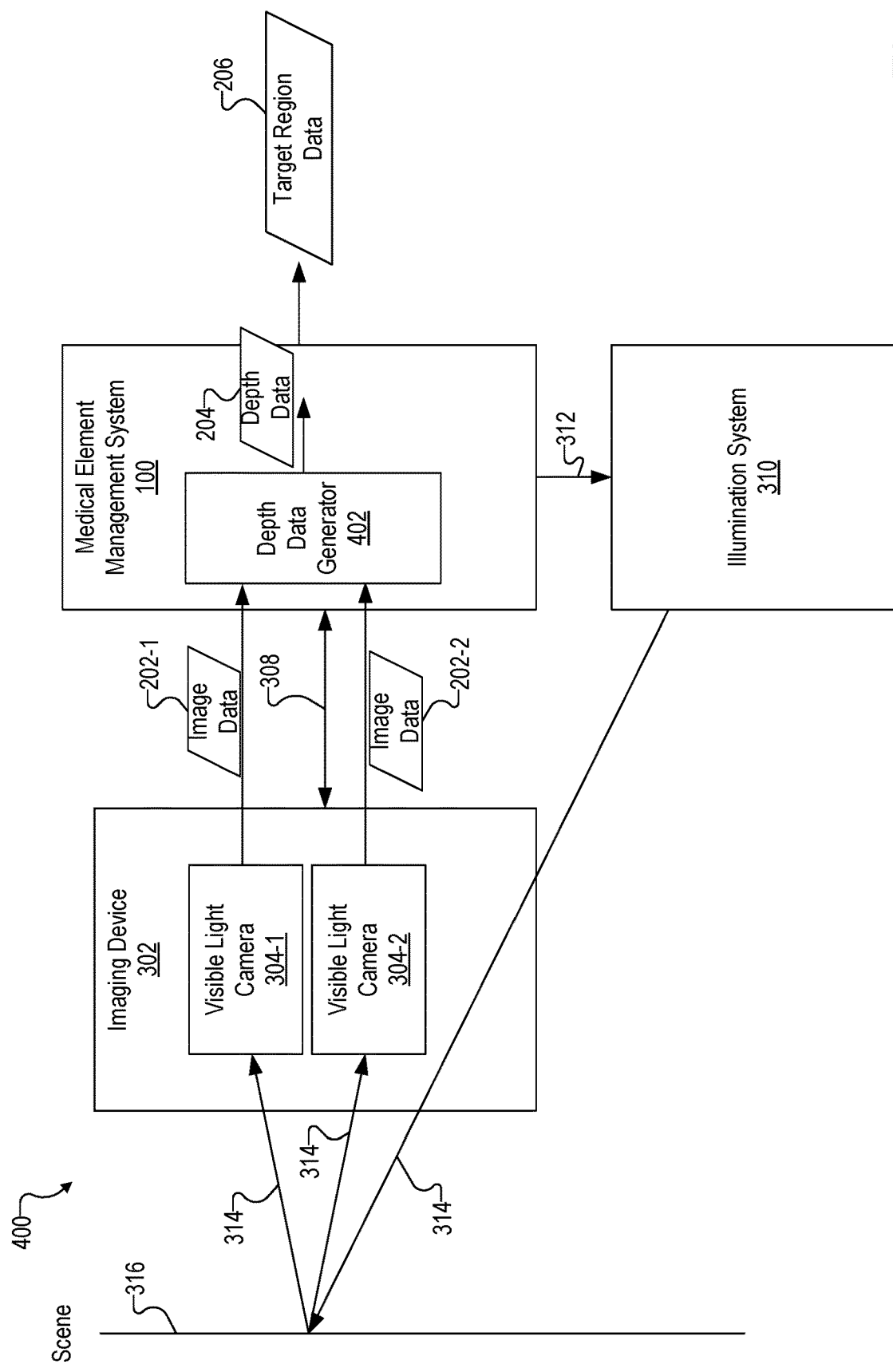
FIG. 4 illustrates an exemplary configuration in which a depth sensor is implemented by visible light cameras according to principles described herein.

FIG. 4 illustrates an exemplary configuration 400 in which depth sensor 402 is implemented by visible light cameras 304-1 and 304-2 included in imaging device 302. In configuration 400, system 100 may obtain depth data 204 by directing camera 304-1 to acquire a first image (e.g., a first two-dimensional image) of an internal space of a patient, directing camera 304-2 to acquire a second image (e.g., a second two-dimensional image) of the internal space of the patient, and generating, based on the first and second images, the depth map represented by depth data 204.

In FIG. 4, the first image acquired by camera 304-1 is represented by image data 202-1 and the second image acquired by camera 304-2 is represented by image data 202-2. As shown, image data 202-1 and 202-2 are transmitted to a depth data generator 402 implemented by system 100. Depth data generator 402 may use any visible image-based technique to determine depth data 204 based on image data 202-1 and 202-2.

Other configurations of imaging device 302 are possible in accordance with the systems and methods described herein. For example, imaging device 302 may include multiple cameras 304 and/or multiple depth sensors 306. To illustrate, imaging device 302 may include two cameras 304 in combination with a separate depth sensor 306. In these embodiments, depth data may be generated based on the images acquired by both cameras 304. Depth data generated by depth sensor 304 may be used to fine tune or otherwise enhance the depth data generated based on the images acquired by both cameras 304.

Figure 5:
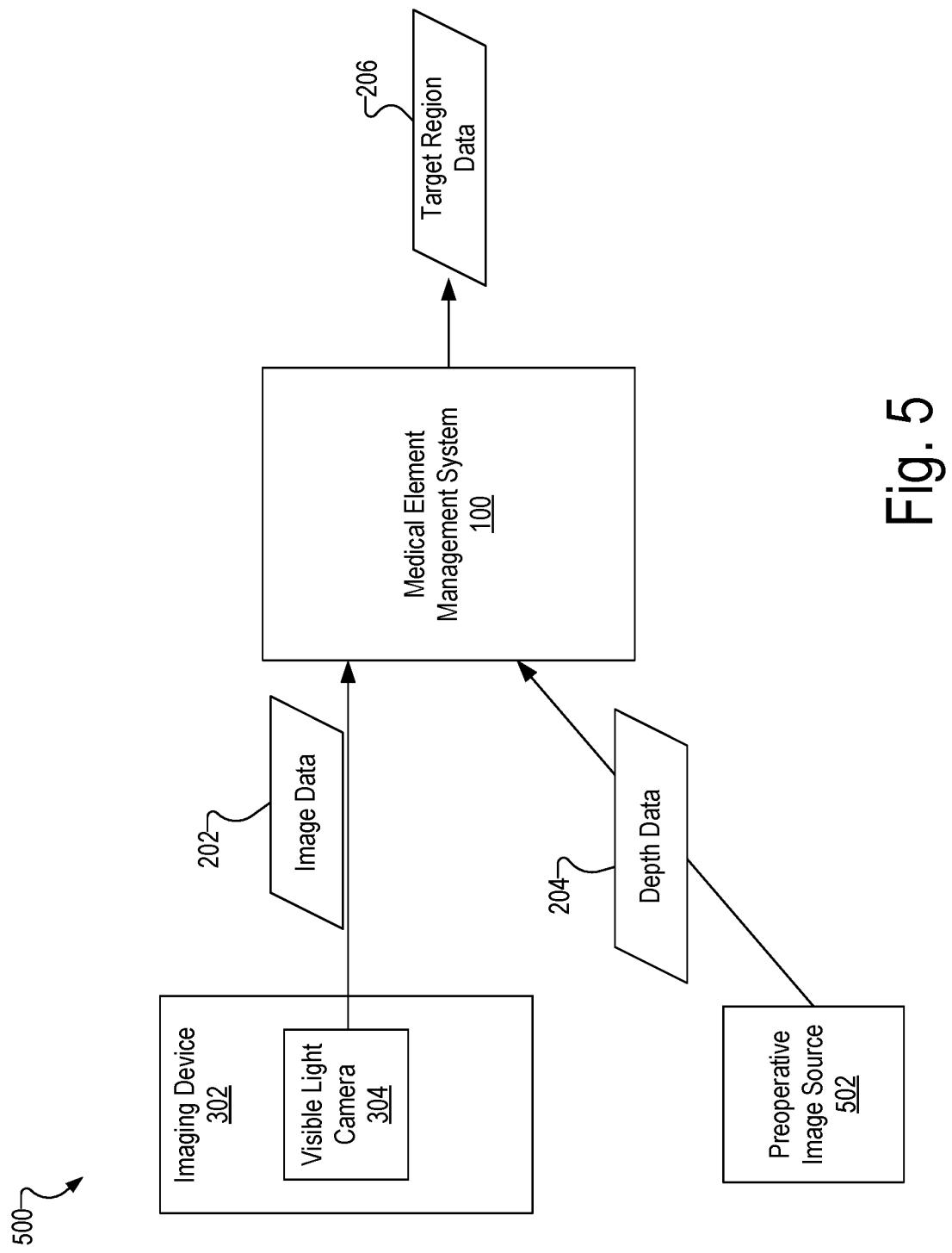
FIG. 5 shows an exemplary configuration in which a system obtains depth data from a preoperative image source according to principles described herein.

In some examples, system 100 may obtain depth data 204 by accessing a preoperative image registered to the image from a source other than imaging device 204. For example, FIG. 5 shows an exemplary configuration 500 in which system 100 obtains depth data 204 from a preoperative image source 502. Source 502 may be implemented by a computer-aided tomography (CT) scanner, a magnetic resonance imaging (MRI) device, an ultrasound device, a three-dimensional scanning (LIDAR) device, and/or any other suitable alternative imaging device configured to generate a preoperative image of the patient. The preoperative image may be registered with the image represented by image data 202 and thereby provide depth data 204.

System 100 may identify the target region based on image data 202 and depth data 204 in any suitable manner. For example, based on image data 202 and depth data 204, system 100 may identify a region within the image represented by image data 202 that depicts tissue in need of being covered by the physical medical element and then designate the identified region as the target region.

System 100 may identify a region of an image that depicts tissue in need of being covered by the physical medical element in any suitable manner. For example, based on image data 202 and depth data 204, system 100 may segment the image (e.g., by classifying different portions of the image as corresponding to different types of tissue) and identify the region based on the segmentation.

Additionally or alternatively, system 100 may identify a region that depicts tissue in need of being covered by the physical medical element by inputting image data 202 and depth data 204 into a machine learning model configured to identify a tissue anomaly. The machine learning model may be trained and/or used in any suitable manner.

In some examples, system 100 may determine a stage within a surgical procedure being performed with respect to the patient and further based the identification of the region that depicts tissue in need of being covered by the physical medical element on the determined stage. For example, system 100 may receive input from a surgeon that the surgeon is attempting to locate a tissue defect within the patient by scanning an internal space of the patient with an imaging device. Based on this input, system 100 may initiate a region identification heuristic that utilizes image data 202 and depth data 204 to automatically identify a region within the image acquired by imaging device that depicts tissue in need of being covered by the physical medical element.

Once the target region that depicts an anatomical surface to be covered by the physical medical element is identified, system 100 may instruct a display device to render a virtual medical element representative of the physical medical element over the identified target region within the image. This may be performed in any suitable manner.

Figure 6:
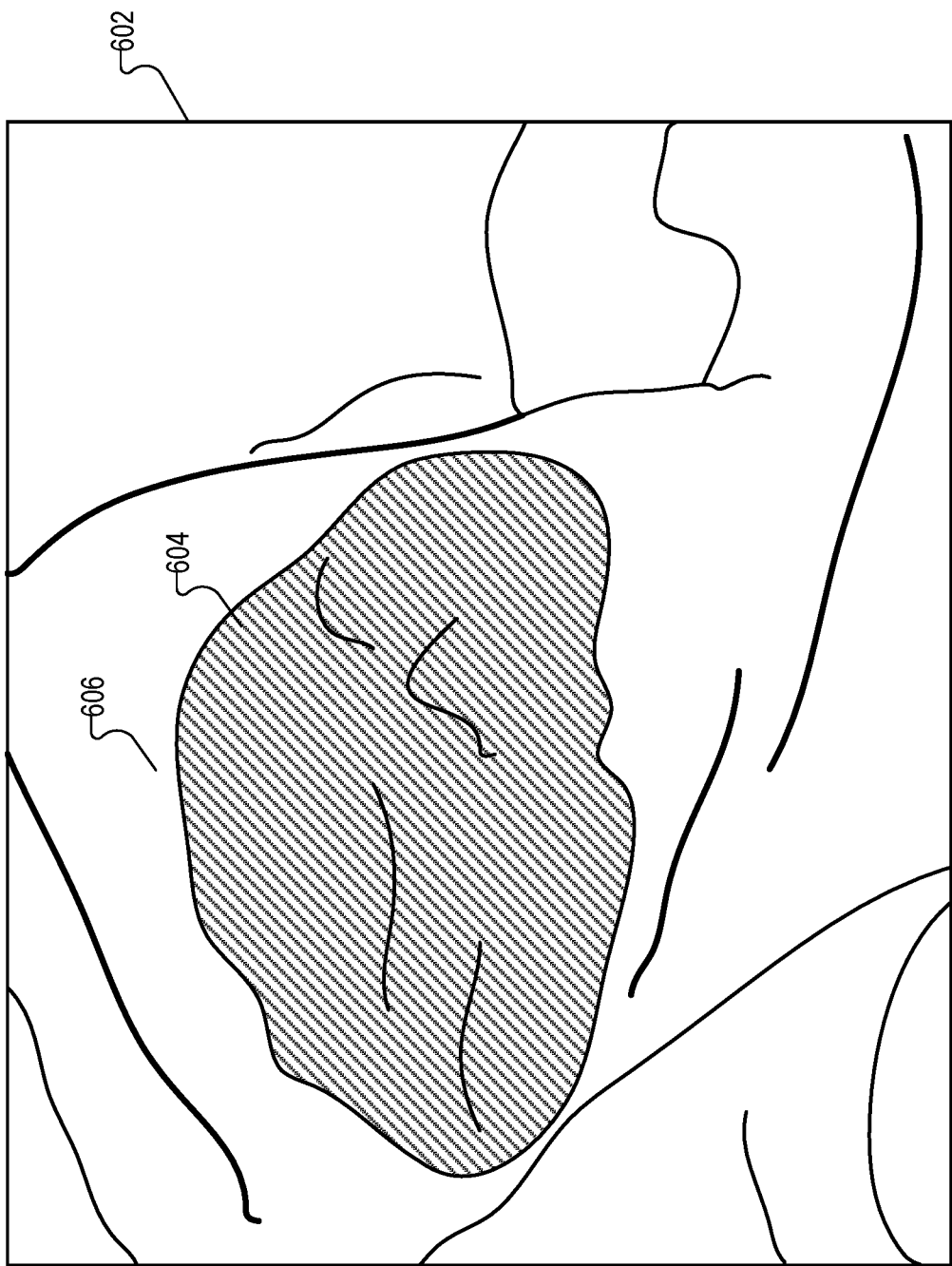
FIG. 6 shows an exemplary image that may be captured by an imaging device according to principles described herein.

By way of illustration, FIG. 6 shows an exemplary image 602 that may be captured by an imaging device aimed at an internal space of a patient and that may be represented by image data 202. As shown, image 602 depicts a tissue defect 604 surrounded by non-defective tissue 606. Tissue defect 604 may be a hernia, cut, or other type of lesion. Non-defective tissue 606 may include, for example, healthy tissue not affected by tissue defect 604.

System 100 may, based on image data 202 and/or depth data 204, identify a target region within image 602 that depicts an anatomical surface that is to be covered by a physical medical element. This may be performed in any of the ways described herein. In some examples, the anatomical surface to be covered by the physical medical element includes at least a portion of tissue defect 604. The anatomical surface to be covered by the physical medical element may, in some instances, also include at least a portion of non-defective tissue 606. For example, the anatomical surface to be covered by the physical medical element may include the entire tissue defect 604 and an overlap region made up of non-defective tissue 606 surrounding tissue defect 604. The overlap region may have any suitable width (e.g., between one and five centimeters), and may be used to attach the physical medical element to the anatomical surface, as described herein.

Tissue defect 604 and the non-defective tissue 606 may have varying relative depths. For example, tissue defect 604 and the non-defective tissue surrounding tissue defect 604 may have various ridges, peaks, valleys, contours, and/or otherwise uneven surfaces. However, such variations in depth may not be visually ascertainable within image 602, especially if image 602 is two-dimensional. Hence, as described herein, system 100 may take such depth variations into account when determining the physical dimensions of the physical medical element that will be cover tissue defect 604 and the overlap region made up of non-defective tissue 606 surrounding tissue defect 604.

Figure 7:
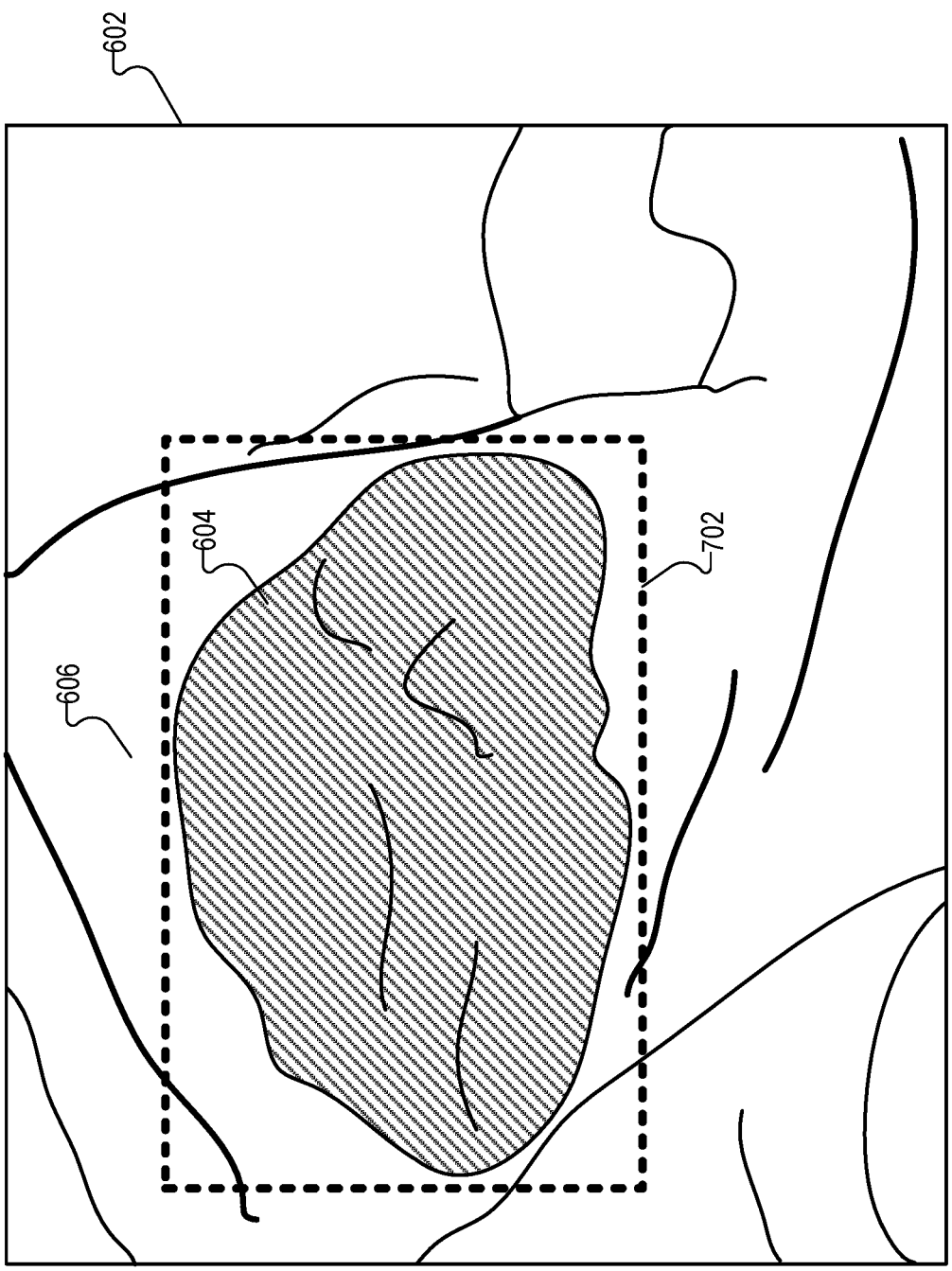
FIGS. 7-9 show an exemplary virtual medical element rendered over an identified target region within an image according to principles described herein.

System 100 may instruct the display device to render a virtual medical element representative of the physical medical element over the identified target region within image 602. For example, FIG. 7 shows an exemplary virtual medical element 702 rendered over the identified target region within image 602. In the example of FIG. 7, virtual medical element 702 includes the dashed line as well as a region enclosed by the dashed line. Moreover, in the example of FIG. 7, the identified target region corresponds directly with (i.e., is completely covered by) virtual medical element 702.

While virtual medical element 702 is illustrated as being a dashed rectangle positioned over tissue defect 604 and a portion of non-defective tissue 606, it will be recognized that virtual medical element 702 may alternatively be rendered in any other suitable manner. For example, virtual medical element 702 may be at least partially transparent to allow visualization by the user of the target region and/or tissue defect 604 while virtual medical element 702 is rendered over the target region.

While virtual medical element 702 is rendered over the target region, a user may provide user input that sets a pose and/or size of virtual medical element 702. For example, if the user determines that the initially determined pose and size of virtual medical element 702 is adequate (e.g., if virtual medical element 702 sufficiently covers the depiction of tissue defect 604), the user may provide user input that confirms that the pose and size of virtual medical element 702 are correct. Such user input may be provided in any suitable manner. For example, such user input may be provided by the user selecting an option displayed in image 602, by the user selecting a user input button on a component of a computer-assisted surgical system, by the user providing a verbal command, and/or in any other manner.

In some cases, the user may determine that the initially determined pose and/or size of virtual medical element 702 needs further refinement. For example, the user may desire to enlarge or shrink virtual medical element 702, reposition one or more edges of virtual medical element 702, and/or otherwise adjust a pose and/or size of virtual medical element 702. In these cases, the user input that sets the pose and/or size of virtual medical element 702 may include one or more user input commands that adjust the pose and/or size of virtual medical element 702. Such user input may be provided in any suitable manner. For example, the user input may be provided by the user interacting with virtual handles displayed as part of virtual medical element 702, providing one or more input commands by way of a graphical user interface within which image 602 is included, providing one or more keyboard or other input device commands, and/or in any other suitable manner. System 100 may dynamically adjust, in response to receiving the user input that adjusts the pose and/or size of virtual medical element 702, the rendering of virtual medical element 702 in substantially real time to depict at least one of the pose and the size of the virtual medical element as adjusted by the user input.

Figure 8:
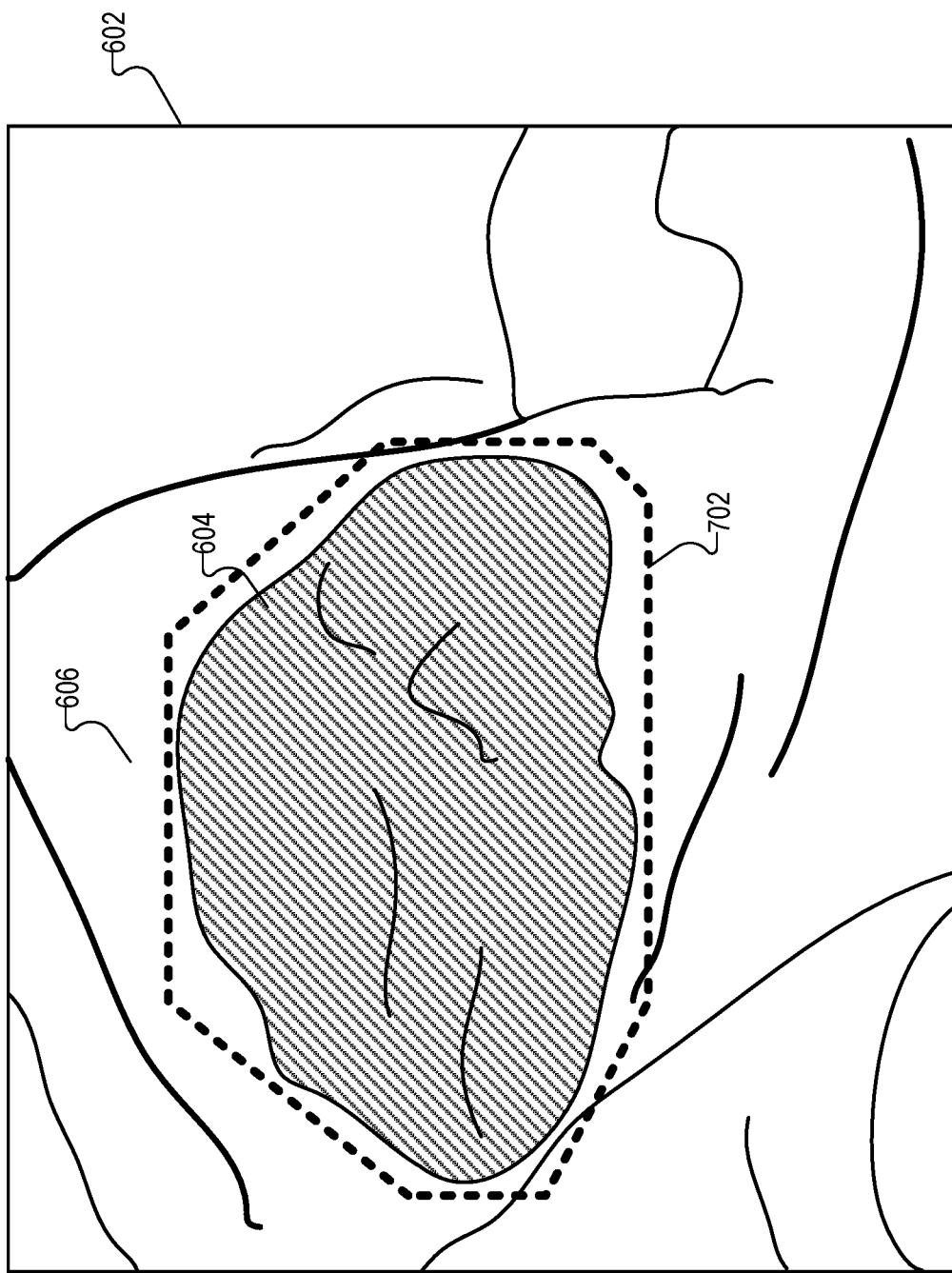

To illustrate, FIG. 8 shows virtual medical element 702 after a user has adjusted a shape (and therefore size) of virtual medical element 702. As shown, the shape and size of virtual medical element 702 as illustrated in FIG. 8 conforms more closely with the actual shape and size of tissue defect 604 than did virtual medical element 702 prior to being adjusted by the user (FIG. 7).

In some examples, the initial shape of virtual medical element 702 is a standard size used for a particular type of physical medical element. For example, the initial shape of virtual medical element 702 may be rectangular, as shown in FIG. 7, for physical medical elements that are typically rectangular in shape.

Figure 9:
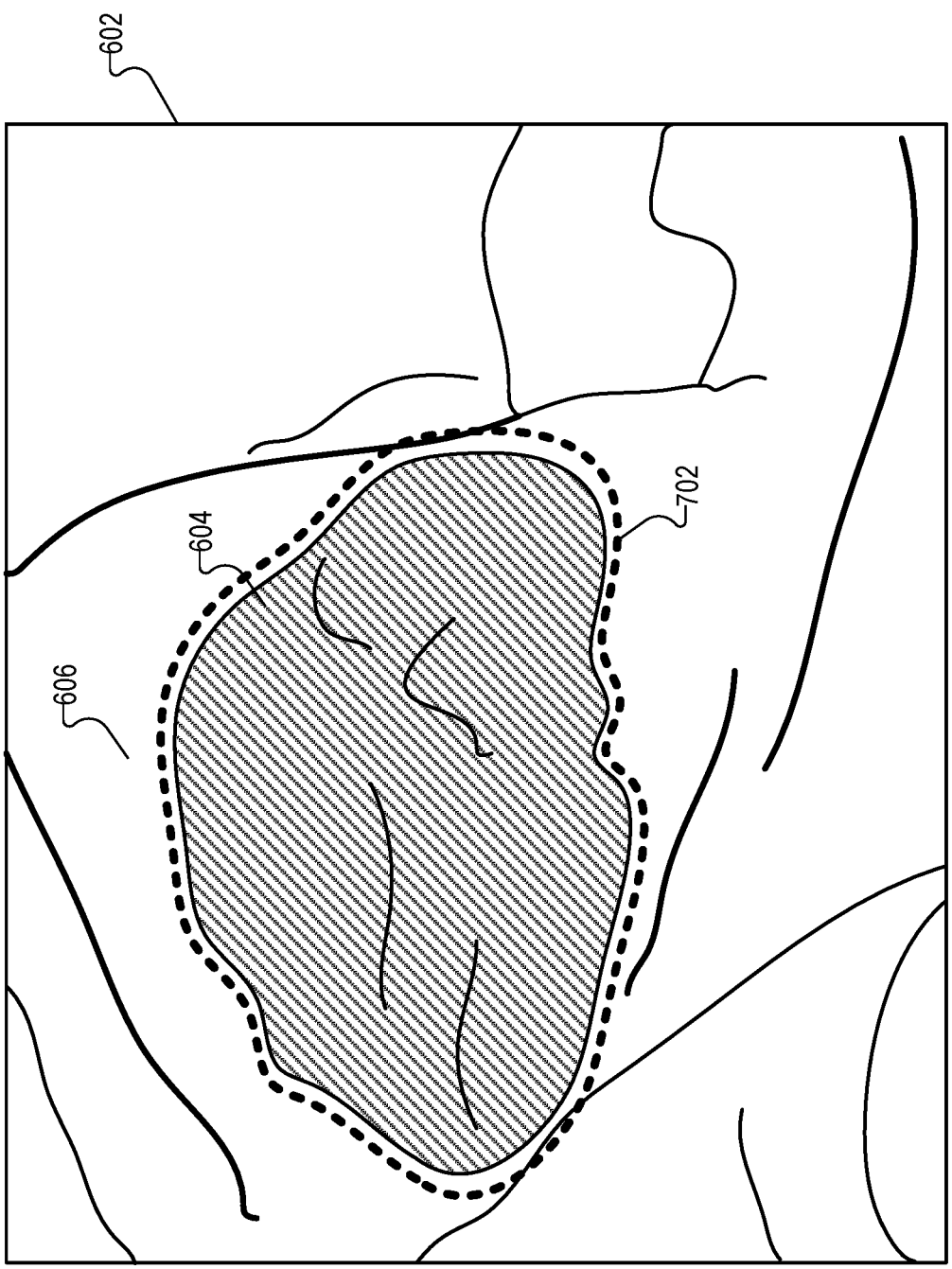

Alternatively, the initial shape of virtual medical element 702 may conform more closely with the actual shape of the anatomical surface to be covered by the physical medical element. For example, FIG. 9 shows an exemplary implementation where virtual medical element 702 has a contoured shape that follows an outer edge of tissue defect 604.

The initial shape of virtual medical element 702 may be determined automatically based on one or more attributes of the physical medical element that is to cover the anatomical surface. Additionally or alternatively, the initial shape of virtual medical element 702 may be specified by a user by providing one or more user input commands.

Figure 10:
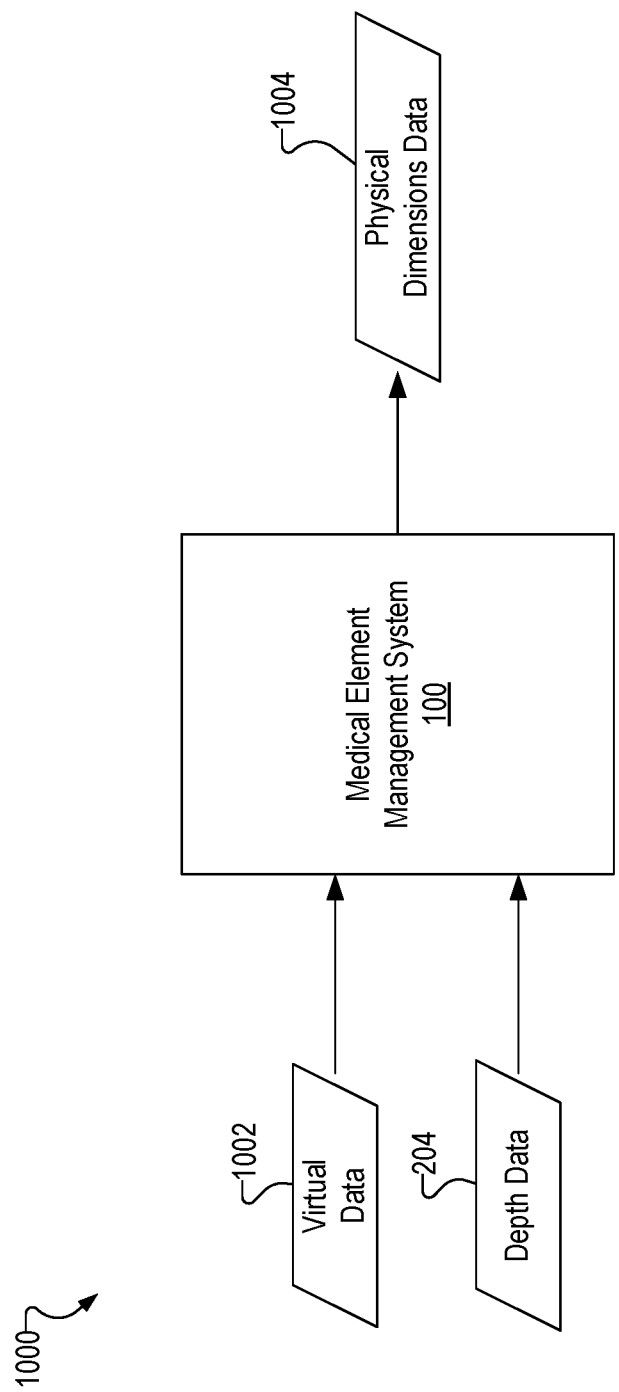
FIGS. 10-11 illustrate exemplary configurations in which a system generates physical dimensions data according to principles described herein.

Based on the user input that sets the pose and/or size of virtual medical element 702 and on depth data 204, system 100 may determine physical dimensions for the physical medical element that is to cover the anatomical surface. For example, FIG. 10 illustrates an exemplary configuration 1000 in which system 100 accesses virtual data 1002 and depth data 204 and generates physical dimensions data 1004 based on virtual data 1002 and depth data 204. Virtual data 1002 may be representative of the pose, size, and/or positioning of virtual medical element 702 as set by the user. Depth data 204, as explained herein, is representative of a depth map for the internal space depicted in image 602. Physical dimensions data 1004 is representative of physical dimensions for the physical medical element as determined by system 100. As described herein, the physical dimensions may represent a surface area for the physical medical element.

System 100 may generate physical dimensions data 1004 based on virtual data 1002 and depth data 204 in any suitable manner. For example, system 100 may identify, based on the pose and the size of the virtual medical element as represented by virtual data 1002, a plurality of pixels within image 602 that are covered by virtual medical element 702. System 100 may determine a two-dimensional pixel area of the plurality of pixels. System 100 may determine, based on depth data 204, depth values for each of the plurality of pixels that are covered by virtual medical element 702. Based on the two-dimensional pixel area and the depth values, system 100 may determine a surface area and/or other dimensions of the anatomical surface to be covered by the physical medical element. System 100 may base the physical dimensions of the physical medical element on the surface area of the anatomical surface. Each of these operations may be performed in any suitable manner.

As mentioned, the systems and methods described herein may be used to determine physical dimensions for a mesh patch used to cover a hernia. As another example, virtual medical element 702 may be representative of a fastener (e.g., a clip or staple) and placed over an image of two tissue sections that are to be fastened together. Based on a sizing and/or change in pose of virtual medical element 702, system 100 may determine physical dimensions for an actual fastener that is to be used to fasten the two tissue sections. As another example, virtual medical element 702 may be representative of bone putty or another type of material that is to be used to fill in a void in a bone. Based on a sizing and/or change in pose of virtual medical element 702, system 100 may determine physical dimensions (e.g., a volume) for actual bone putty that is to be used to fill in the void. These examples are merely illustrative of the many different ways in which system 100 may determine physical dimensions for a medical element that is to be introduced into a patient.

Because of the variations in depth that the anatomical surface may have, the surface area for the physical medical element as defined by the physical dimensions of virtual medical element 702 may, in some cases, be greater than a physical area represented by the two-dimensional pixel area. For example, the physical medical element may be made out of a material configured to "shrink wrap" or otherwise adhere to all of the surface area of the anatomical surface. In this example, if the anatomical surface has protruding ridge that needs to be covered by the physical medical element, this variation in depth may result in the surface area defined by the physical dimensions of the physical medical element as determined by system 100 being larger than a physical area represented by the two-dimensional pixel area of virtual medical element 702.

Figure 11:
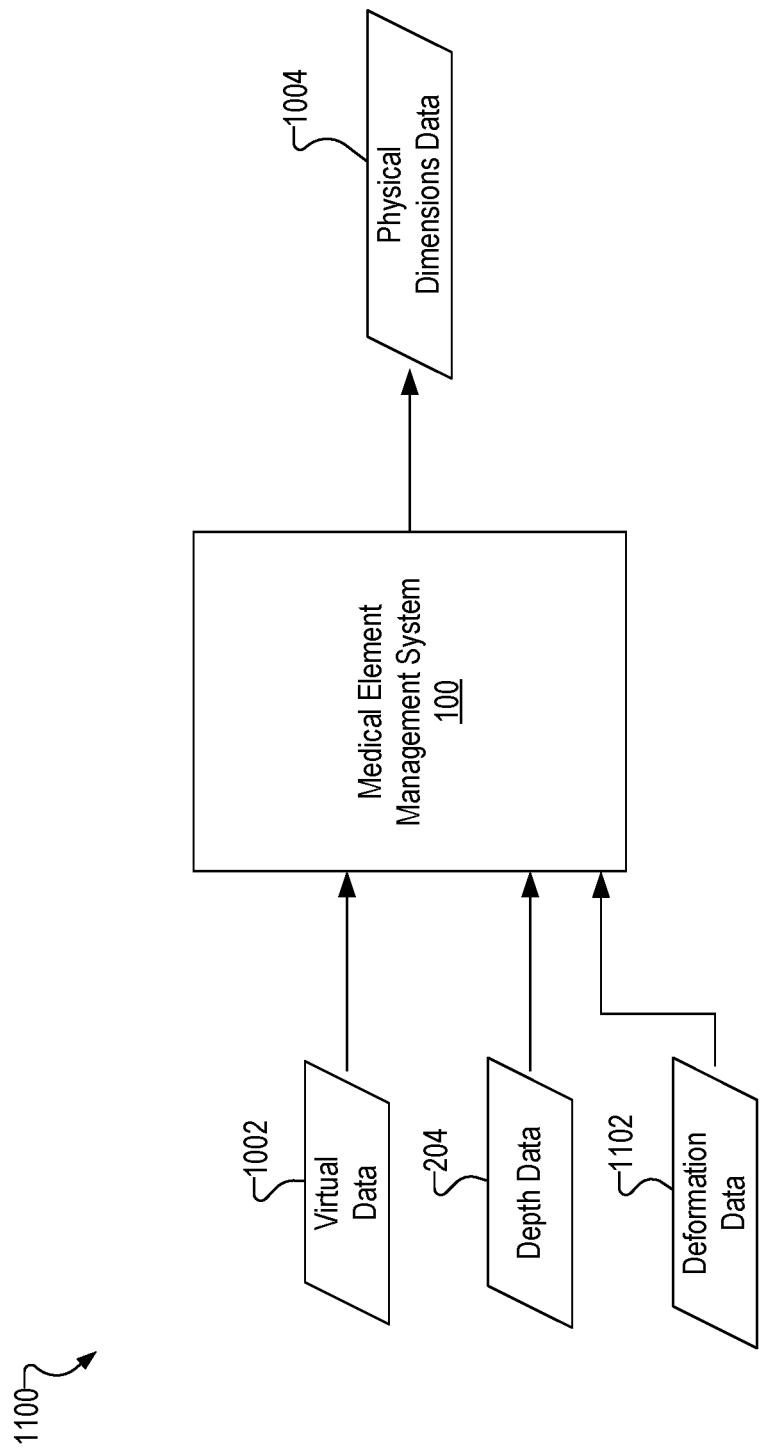

FIG. 11 shows an exemplary configuration 1100 in which system 100 further bases the generation of physical dimensions data 1004 on deformation data 1102 in addition to virtual data 1002 and depth data 204. Deformation data 1102 is representative of a deformation model of the physical medical element. The deformation model may indicate one or more physical attributes of a physical medical element that affect an ability of the physical medical element to deform (e.g., stretch, compress, etc.) in response to force applied to the physical medical element. For example, the deformation model may indicate a type of material from which the physical medical element is made, a tensile strength of the material, and/or any other metric representative of deformation as may serve a particular implementation.

System 100 may determine the physical dimensions of the physical medical element based on deformation data 1102 in any suitable manner. For example, if deformation data 1102 indicates that the physical medical element is relatively resistant to stretching, system 100 may specify that the physical dimensions are to be relatively smaller than a different type of physical medical element that exhibits a high degree of stretching.

System 100 may obtain deformation data 1102 in any suitable manner. For example, system 100 may maintain or access a database that includes deformation data 1102 for various types of physical medical elements. System 100 may ascertain which particular physical medical element is to be used to cover the anatomical surface by receiving user input indicating which physical medical element is to be used, automatically determining which physical medical element is to be used based on tracked tendencies of a particular user and/or a particular type of surgical procedure being performed, and/or in any other suitable manner.

System 100 may output data representative of the physical dimensions in any suitable manner. For example, system 100 may output data representative of the physical dimensions by displaying the physical dimensions within image 602 or within any other suitable user interface. Additionally or alternatively, system 100 may output data representative of the physical dimensions by outputting physical measurements (e.g., a width and length in centimeters) of the physical medical element. Additionally or alternatively, system 100 may output data representative of the physical dimensions by outputting data representative of a pattern to be used to cut the physical medical element out of a material.

In some examples, system 100 may project virtual medical element 702 onto a physical material from which the physical medical element is to be cut. In this manner, virtual medical element 702 may guide a user in cutting the physical medical element out of the physical material.

Figure 12:
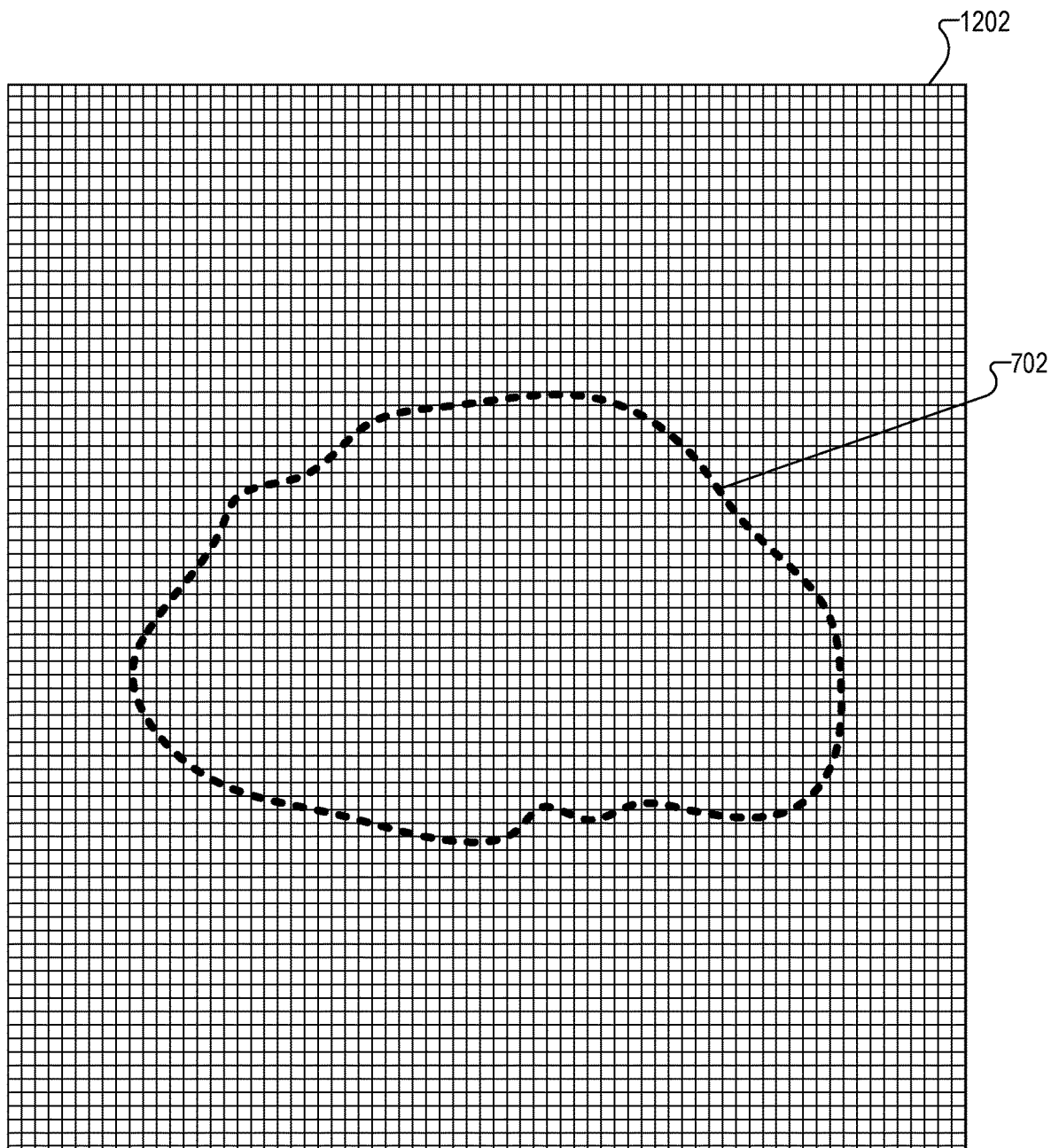
FIG. 12 shows an exemplary physical material from which a physical medical element is to be cut according to principles described herein.

To illustrate, FIG. 12 shows an exemplary physical material 1202 from which the physical medical element is to be cut. In the example of FIG. 12, physical material 1202 is a mesh material from which patches for hernias and/or other types of tissue defects may be cut. As shown, system 100 has projected the virtual medical element 702 onto physical material 1202. Virtual medical element 702 may be projected onto physical material 1202 in any suitable manner.

Once a physical medical element is ready to be introduced into the patient, system 100 may be configured to provide placement guidance configured to guide and/or assist a user in placing the physical medical element on the anatomical surface. This placement guidance may be provided in a number of different ways.

Figure 13:
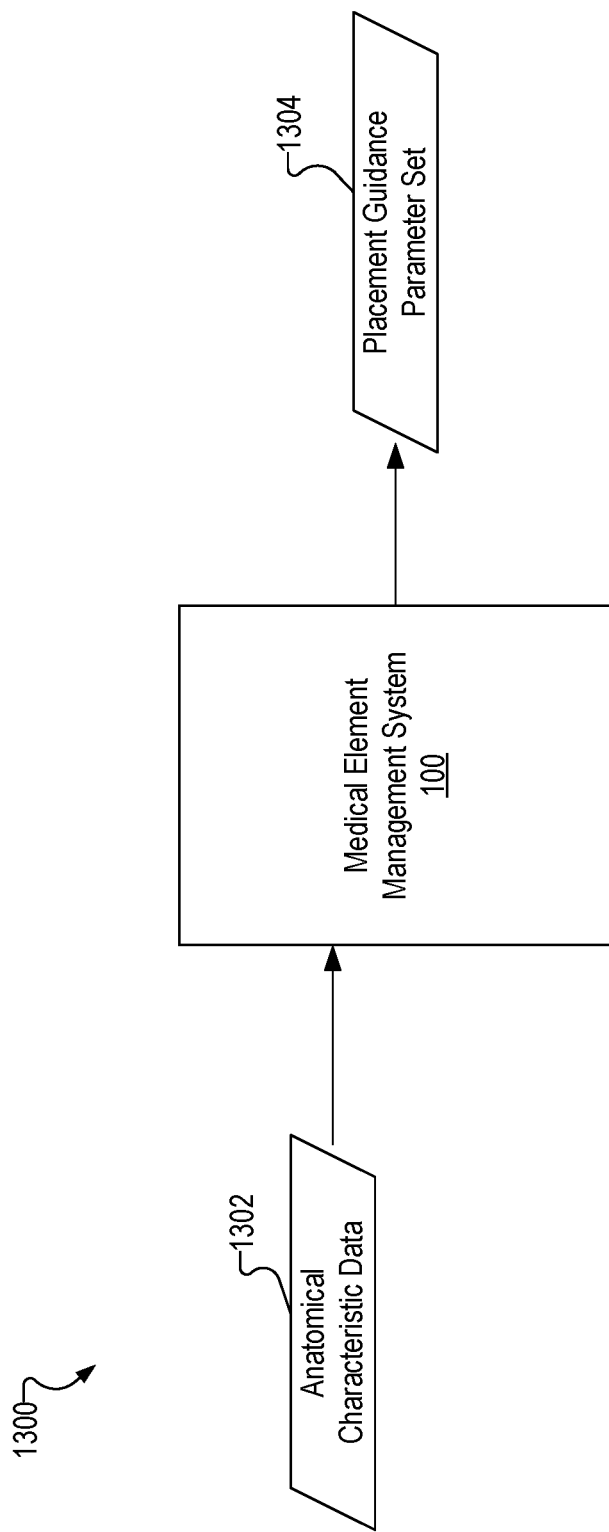
FIGS. 13-14 illustrate exemplary configurations in which a system determines a placement guidance parameter set according to principles described herein.

For example, FIG. 13 illustrates exemplary configuration 1300 in which system 100 obtains anatomical characteristic data 1302 representative of a characteristic associated with an anatomical surface to be covered by a physical medical element and determines, based on anatomical characteristic data 1302, a placement guidance parameter set 1304. Placement guidance parameter set 1304 includes one or more parameters configured to guide a placement of the physical medical element on the anatomical surface with one or more surgical instruments controlled by a computer-assisted surgical system.

Anatomical characteristic data 1302 may be representative of one or more characteristics associated with the anatomical surface to be covered by the physical medical element. For example, anatomical characteristic data 1302 may be representative of a type of tissue that constitutes the anatomical surface, a size of the anatomical surface, and/or a location of the anatomical surface within the patient. These characteristics may affect the way in which the physical medical element is placed on the anatomical surface. For example, if the anatomical surface is located in a vicinity of an organ, system 100 may generate one or more parameters for inclusion in placement guidance parameter set 1304 that indicate that the anatomical surface is near the organ and that may be used to identify a suturing plan for attaching the physical medical element to the anatomical surface in a manner that does not damage or otherwise affect the organ. As another example, if the tissue that constitutes the anatomical surface is relatively weak, system 100 may generate one or more parameters for inclusion in the placement guidance parameter set 1304 that may be used to increase the relative number of sutures are used to attach the physical medical element to the anatomical surface.

System 100 may obtain anatomical characteristic data 1302 in any suitable manner. For example, system 100 may obtain anatomical characteristic data 1302 by accessing image data 202, obtaining depth data 204, and determining, based on image data 202 and depth data 204, anatomical characteristic data 1302. To illustrate, image data 202 and depth data 204 may be used to determine a location of the anatomical surface, a size of the anatomical surface, and/or any other characteristic of the anatomical surface.

In some examples, system 100 may use image data 202 and depth data 204 to segment the image represented by image data 202. The segmentation may include classifying different portions of the image as corresponding to different items (e.g., types of tissue). Based on the segmentation, system 100 may determine one or more characteristics of the anatomical surface, such as tissue type, etc.

Figure 14:
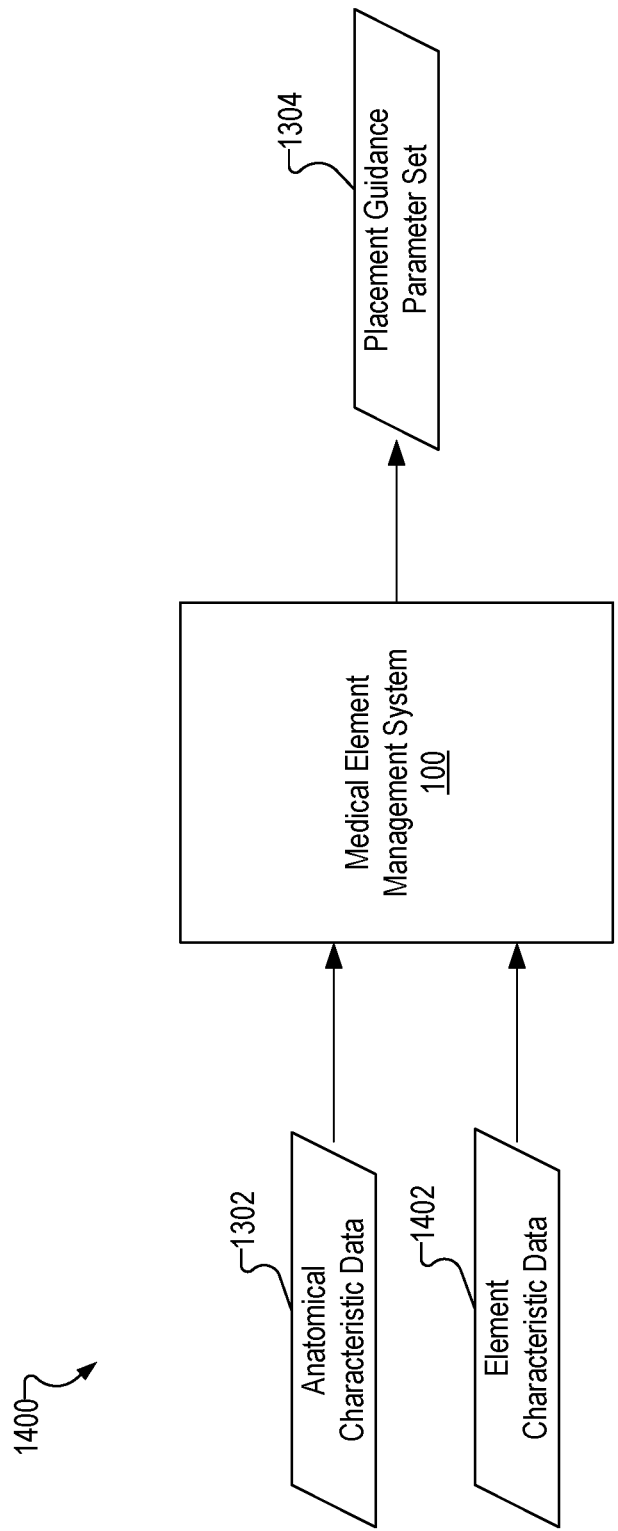

FIG. 14 illustrates exemplary configuration 1400 in which system 100 obtains element characteristic data 1402 in addition to anatomical characteristic data 1302. As shown, in configuration 1400, system 100 generates placement guidance parameter set 1304 based on both anatomical characteristic data 1302 and element characteristic data 1402. In alternative examples, system 100 generates placement guidance parameter set 1304 based only on element characteristic data 1402 (and not anatomical characteristic data 1302).

Element characteristic data 1402 is representative of one or more characteristics associated with the physical medical element that will cover the anatomical surface. For example, element characteristic data 1402 may be representative of physical dimensions of the physical medical element, a type of material used for the physical medical element, a tensile strength of the physical medical element, and/or a deformation characteristic of the physical medical element.

System 100 may access element characteristic data 1402 in any suitable manner. For example, system 100 may maintain or access a database that includes element characteristic data 1402. As another example, system 100 may access element characteristic data 1402 by receiving user input representative of the access element characteristic data 1402.

In some examples, placement guidance parameter set 1304 includes one or more parameters configured to specify an optimal orientation for the physical medical element as the physical medical element is being placed on the anatomical surface with one or more surgical instruments controlled by a computer-assisted surgical system. In these examples, system 100 may indicate the optimal orientation for the physical medical element to a user in any suitable manner.

Figure 15:
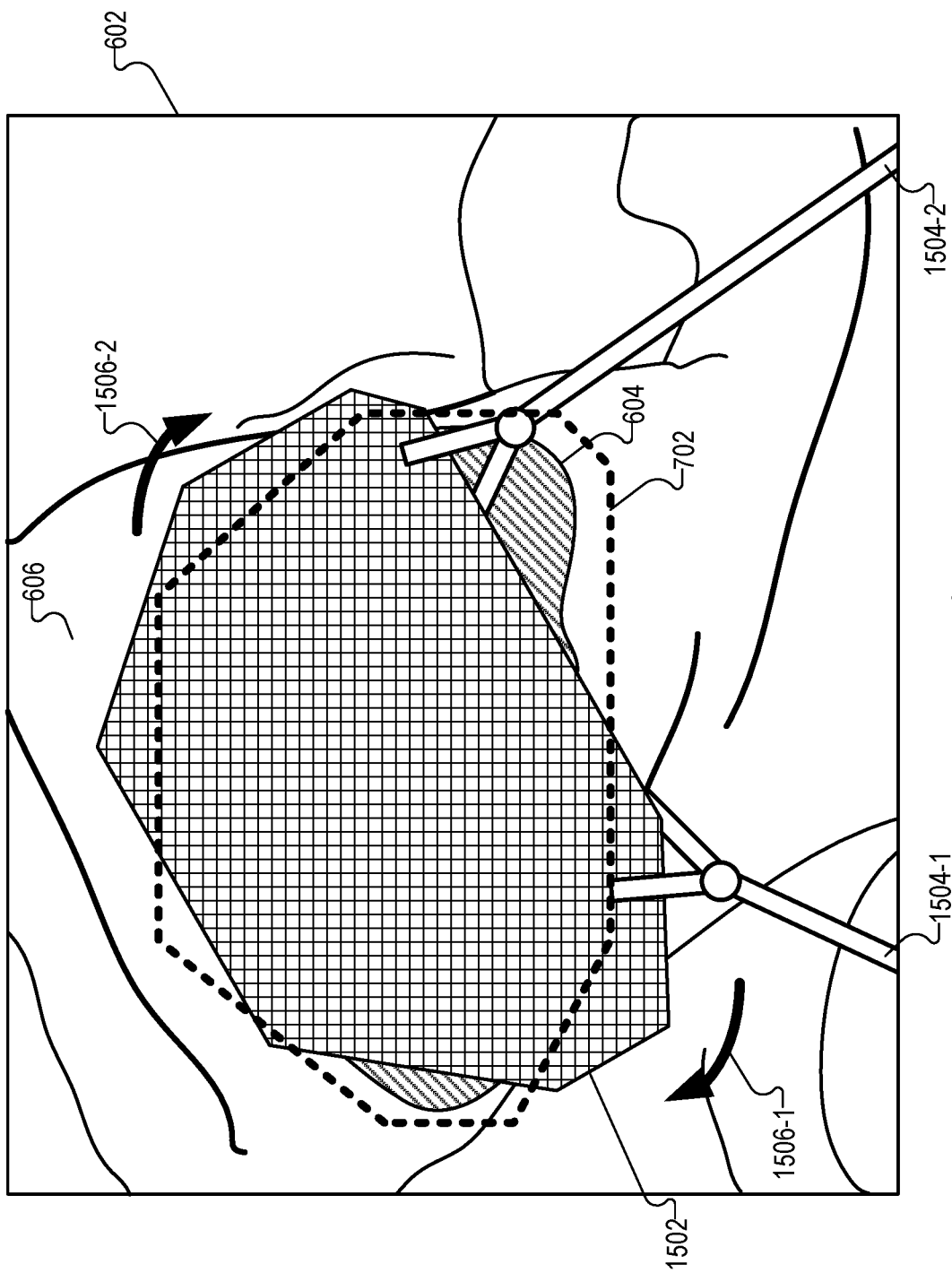
FIGS. 15-16 show an exemplary scenario in which a physical medical element is being placed on an anatomical surface that includes a tissue defect and a portion of non-defective tissue according to principles described herein.

For example, system 100 may be configured to indicate the optimal orientation for the physical medical element to a user by graphically indicating, within an image (e.g., image 602) of the internal space, the optimal orientation. To illustrate, FIG. 15 shows an exemplary scenario in which a physical medical element 1502 is being placed on an anatomical surface that includes tissue defect 604 and a portion of non-defective tissue 606.

As shown, physical medical element 1502 is being placed on the anatomical surface by surgical instruments 1504-1 and 1504-2 ("surgical instruments 1504"). Surgical instruments 1504 may include any suitable grasping tool configured to hold and guide physical medical element 1502 into place. In some examples, surgical instruments 1504 are controlled by a computer-assisted surgical system (e.g., in response to user input commands provided by a surgeon or other user).

As shown, system 100 may render virtual medical element 702 within image 602 while the user is using surgical instruments 1504 to place physical medical element 1502 on the anatomical surface. In this configuration, virtual medical element 702 graphically indicates the optimal orientation of physical medical element. In addition, graphical arrows 1506-1 and 1506-2 may be rendered by system 100 within image 602 to indicate a direction in which the user should rotate physical medical element 1502 to arrive at the optimal orientation. System 100 may additionally or alternatively present any other suitable virtual, audible, and/or graphical assistance indicative of the optimal orientation of physical medical element 1502 as may serve a particular implementation.

In some examples, placement guidance parameter set 1304 includes one or more parameters configured to specify an optimal insertion path within the internal space that surgical instruments 1504 are to follow while bringing physical medical element 1502 from outside the patient to being in contact with the anatomical surface. In these examples, system 100 may indicate the optimal insertion path for physical medical element 1502 to a user in any suitable manner. For example, system 100 may be configured to indicate the optimal insertion path for the physical medical element by graphically indicating, within an image (e.g., image 602) of the internal space, the optimal insertion path. System 100 may additionally or alternatively present any other suitable virtual, audible, and/or graphical assistance indicative of the optimal insertion path as may serve a particular implementation.

The optimal insertion path specified by the one or more parameters in placement guidance parameter set 1304 may be defined such that surgical instruments 1504 and/or physical medical element 1502 avoid collision with tissue and/or other objects (e.g., other surgical instruments) in the internal space while physical medical element 1502 is brought from outside the patient to being in contact with the anatomical surface.

In some examples, placement guidance parameter set 1304 includes one or more parameters configured to specify a suturing plan for suturing physical medical element 1502 to the anatomical surface while the surgical instruments 1504 hold physical medical element 1502 in place on the anatomical surface. The suturing plan may include information specifying a suture pattern to be used to suture physical medical element 1502 to the anatomical surface, a spacing to be used between sutures used to suture physical medical element 1502 to the anatomical surface, a type of thread to be used to suture physical medical element 1502 to the anatomical surface, a length of thread needed to suture physical medical element 1502 to the anatomical surface, and/or any other aspect of a suturing plan as may serve a particular implementation. While exemplary suturing plans are described herein, it will be recognized that placement guidance parameter set 1304 may alternatively include one or more parameters configured to specify any other type of affixation plan that may be used to affix physical medical element 1502 to the anatomical surface.

By way of example, an exemplary suturing plan that may be specified by one or more parameters in placement guidance parameter set 1304 may indicate a recommended suture pattern, suture spacing, thread type, and/or thread length for a particular type of tissue as indicated in anatomical characteristic data 1302, a particular type and/or size of tissue defect 604 as indicated in anatomical characteristic data 1302, a proximity of other objects (e.g., organs) to tissue defect 604 as indicated in anatomical characteristic data 1302, and/or any other characteristic of the anatomical surface as indicated in anatomical characteristic data 1302. Additionally or alternatively, an exemplary suturing plan that may be specified by one or more parameters in placement guidance parameter set 1304 may indicate a recommended suture pattern, suture spacing, thread type, and/or thread length for one or more of the characteristics of physical medical element 1502 as indicated in element characteristic data 1402.

Figure 16:
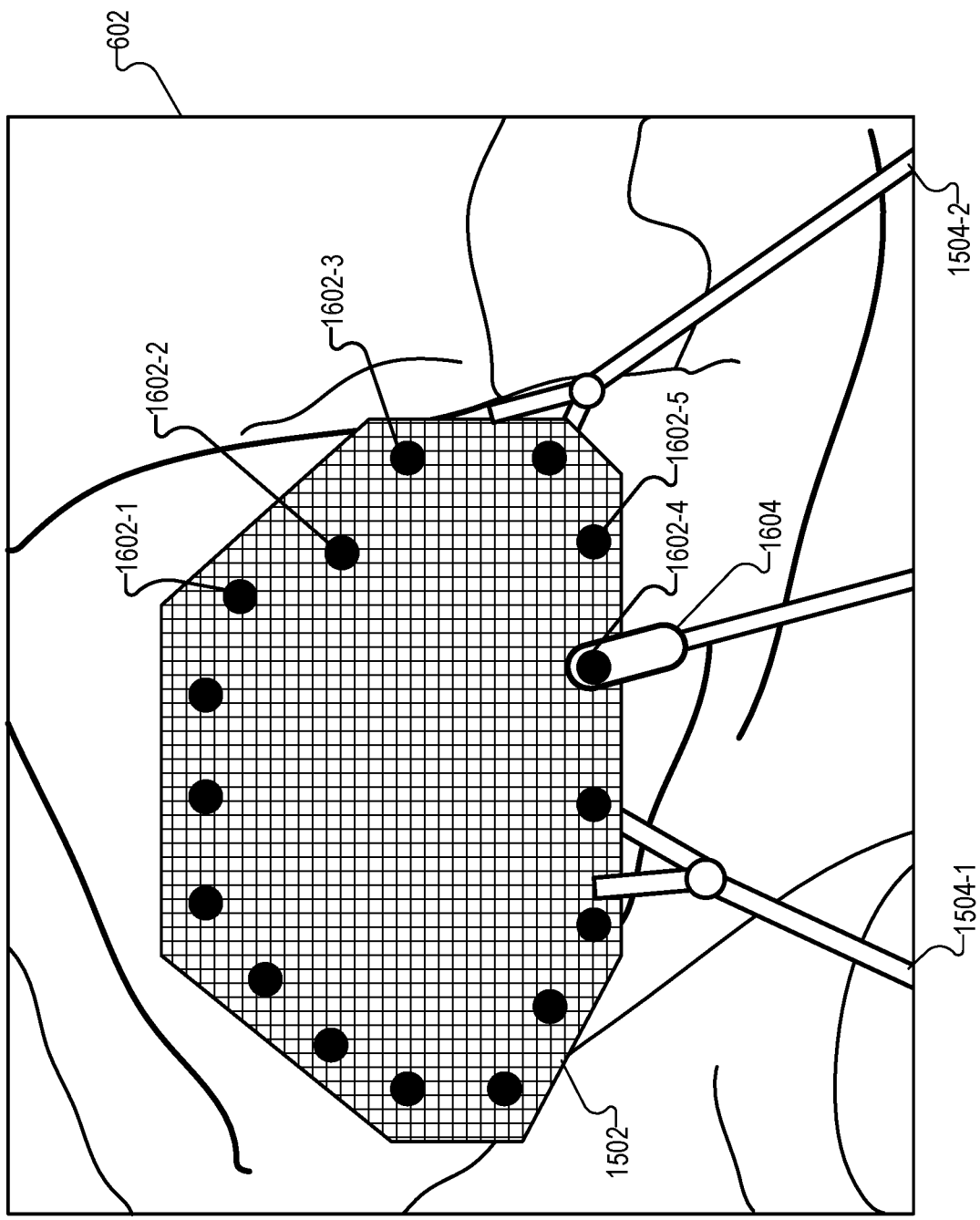

In some examples, system 100 may be configured to graphically indicate the suturing plan within image 602. For example, FIG. 16 shows physical medical element 1502 prior to being sutured to the anatomical surface. System 100 may graphically indicate the suturing plan within image 602 by presenting virtual markers (e.g., virtual markers 1602-1 through 1602-5) representative of locations where sutures are to be placed to attach physical medical element 1502 to the anatomical surface. The position and spacing of each virtual marker 1602 may be determined based on anatomical characteristic data 1302 and/or element characteristic data 1402. For example, the majority of virtual markers 1602 are positioned approximately the same distance from an outer edge of physical medical element 1502. However, in this example, virtual marker 1602-2 is offset with respect to its adjacent virtual markers 1602-1 and 1602-3 (i.e., virtual marker 1602-2 is further away from the edge of physical medical element 1502 than virtual markers 1602-1 and 1602-3). This may be because anatomical characteristic data 1302 may indicate that the tissue in the vicinity of the location on physical medical element 1502 that corresponds to virtual marker 1602-2 is relatively weak, thereby necessitating a larger gap between the suture location and the edge of physical medical element 1502.

In some examples, a user may provide user input configured to modify the suturing plan graphically indicated within image 602. For example, a user may provide input that adjusts a position of one or more of virtual markers 1602, removes a particular virtual marker 1602, adds a new virtual marker, and/or otherwise modifies the suturing plan. In response to this user input, system 100 may dynamically adjust the suturing plan in accordance with the user input. For example, based on a repositioning by a user of a particular virtual marker 1602, system 100 may update an amount of thread needed to perform the suturing, adjust a positioning of a suturing device and/or one or more other surgical instruments, and/or otherwise adjust the suturing plan.

FIG. 16 also shows a suturing device 1604 positioned at a location on physical medical element 1502 that corresponds to a particular virtual marker 1602-4. Suturing device 1604 may be configured to suture physical medical element 1502 to the anatomical surface in any suitable manner. For example, suturing device 1604 may apply a running suture (or any other type of suture) around a perimeter of physical medical element 1502 at various locations corresponding to virtual markers 1602.

In some examples, suturing device 1604 is controlled by a computer-assisted surgical system (e.g., by being connected to a manipulator arm of the computer-assisted surgical system). In these examples, suturing device 1604 may be referred to as a certain type of surgical instrument coupled to and controlled by the computer-assisted surgical system. In alternative examples, suturing device 1604 is not controlled by a computer-assisted surgical system. In these alternative examples, suturing device 1604 may be manually held and/or otherwise controlled by a user.

In cases where suturing device 1604 is controlled by a computer-assisted surgical system, a positioning and/or operation of suturing device 1604 may be set in response to user input (e.g., a user may provide input commands that move and/or operate suturing device 1604). For example, the user may provide input commands that direct the computer-assisted surgical system to move suturing device 1604 from suturing location to suturing location as guided by the suturing plan represented by virtual markers 1602. For example, after suturing device 1604 is used to suture physical medical element 1502 to the anatomical surface at a suture location corresponding to virtual marker 1602-4, the user may provide input commands (e.g., by manipulating master controls that are a part of the computer-assisted surgical system) that cause suturing device 1604 to move to a suture location that corresponds to virtual marker 1602-5. Once at this location, suturing device 1604 may be used to suture physical medical element 1502 to the anatomical surface at the suture location corresponding to virtual marker 1602-5. Such repositioning of suturing device 1604 may alternatively be performed automatically by the computer-assisted surgical system without specific user input that controls a positioning and/or operation of suturing device 1604.

In some examples, system 100 may direct, in accordance with placement guidance parameter set 1304, a computer-assisted surgical system to use one or more surgical instruments (e.g., surgical instruments 1504 and/or suturing device 1604) to automatically place a physical medical element (e.g., physical medical element 1502) on the anatomical surface without a user providing user input that controls a movement of the one or more surgical instrument while the physical medical element is being placed on the anatomical surface by the one or more surgical instruments. For example, system 100 may direct a computer-assisted surgical system to use surgical instruments 1504 to guide physical medical element 1502 to a proper orientation and positioning over the anatomical surface. System 100 may then direct the computer-assisted surgical system to use suturing device 1604 to automatically suture physical medical element 1502 to the anatomical surface.

In some examples, system 100 may track a relative pose of suturing device 1604 and/or surgical instruments 1504 with respect to physical medical element 1502. System 100 may use the tracked pose to direct suturing device 1604 to properly perform the suturing of physical medical element 1502 to the anatomical surface and/or surgical instruments 1504 to properly grasp and hold physical medical element 1502.

Figure 17:
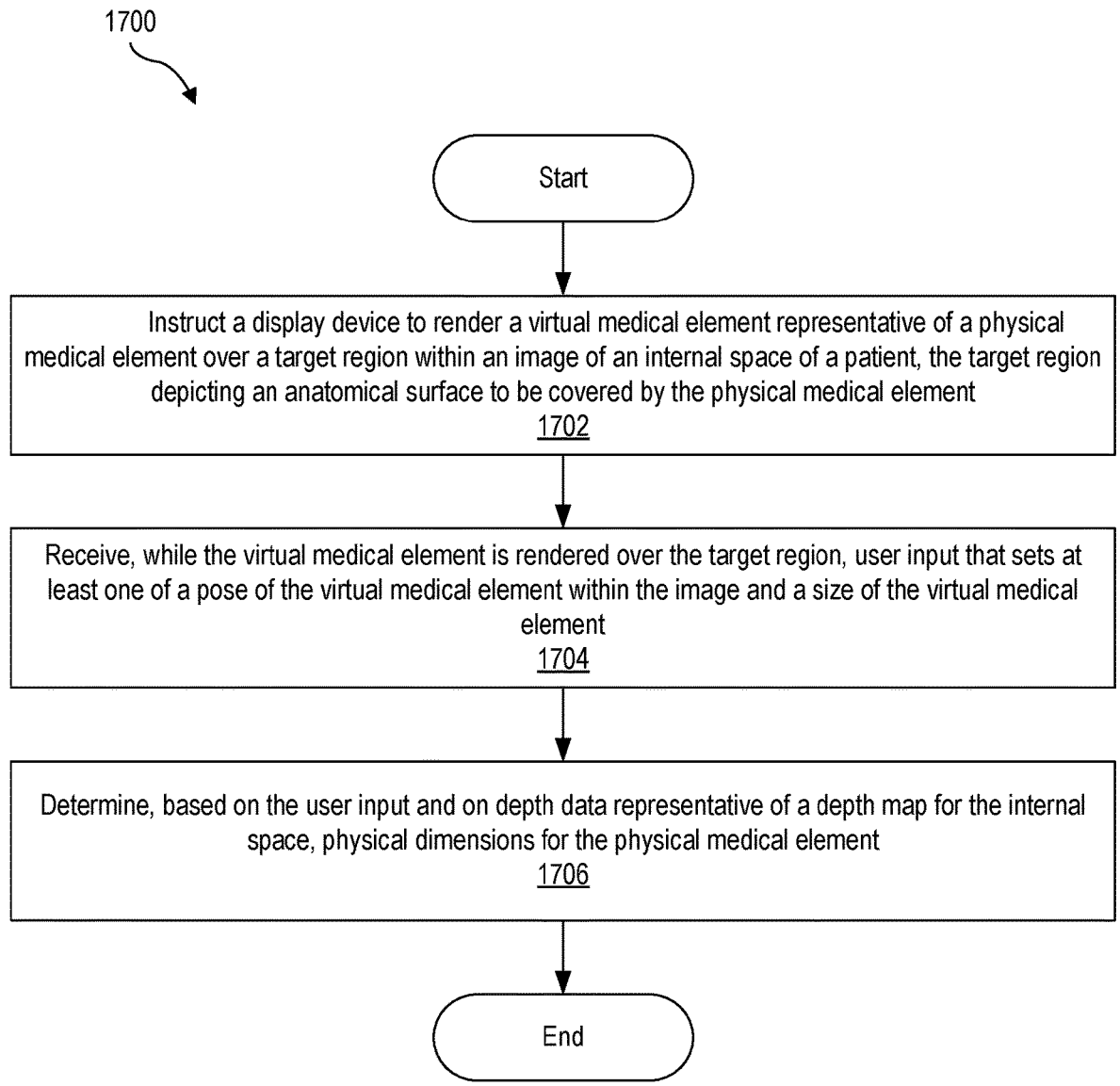
FIGS. 17-20 illustrate exemplary methods according to principles described herein.

FIG. 17 illustrates an exemplary method 1700 that may be performed by a medical element management system (e.g., system 100 and/or any implementation thereof). While FIG. 17 illustrates exemplary operations according to one embodiment, other embodiments may omit, add to, reorder, and/or modify any of the operations shown in FIG. 17.

In operation 1702, a medical element management system instructs a display device to render a virtual medical element representative of a physical medical element over a target region within an image of an internal space of a patient, the target region depicting an anatomical surface to be covered by the physical medical element. Operation 1702 may be performed in any of the ways described herein.

In operation 1704, the medical element management system receives, while the virtual medical element is rendered over the target region, user input that sets at least one of a pose of the virtual medical element within the image and a size of the virtual medical element. Operation 1704 may be performed in any of the ways described herein.

In operation 1706, the medical element management system determines, based on the user input and on depth data representative of a depth map for the internal space, physical dimensions for the physical medical element. In some examples, the physical dimensions may specify a surface area, a volume, or any other suitable dimension for the physical medical element. Operation 1706 may be performed in any of the ways described herein.

Figure 18:
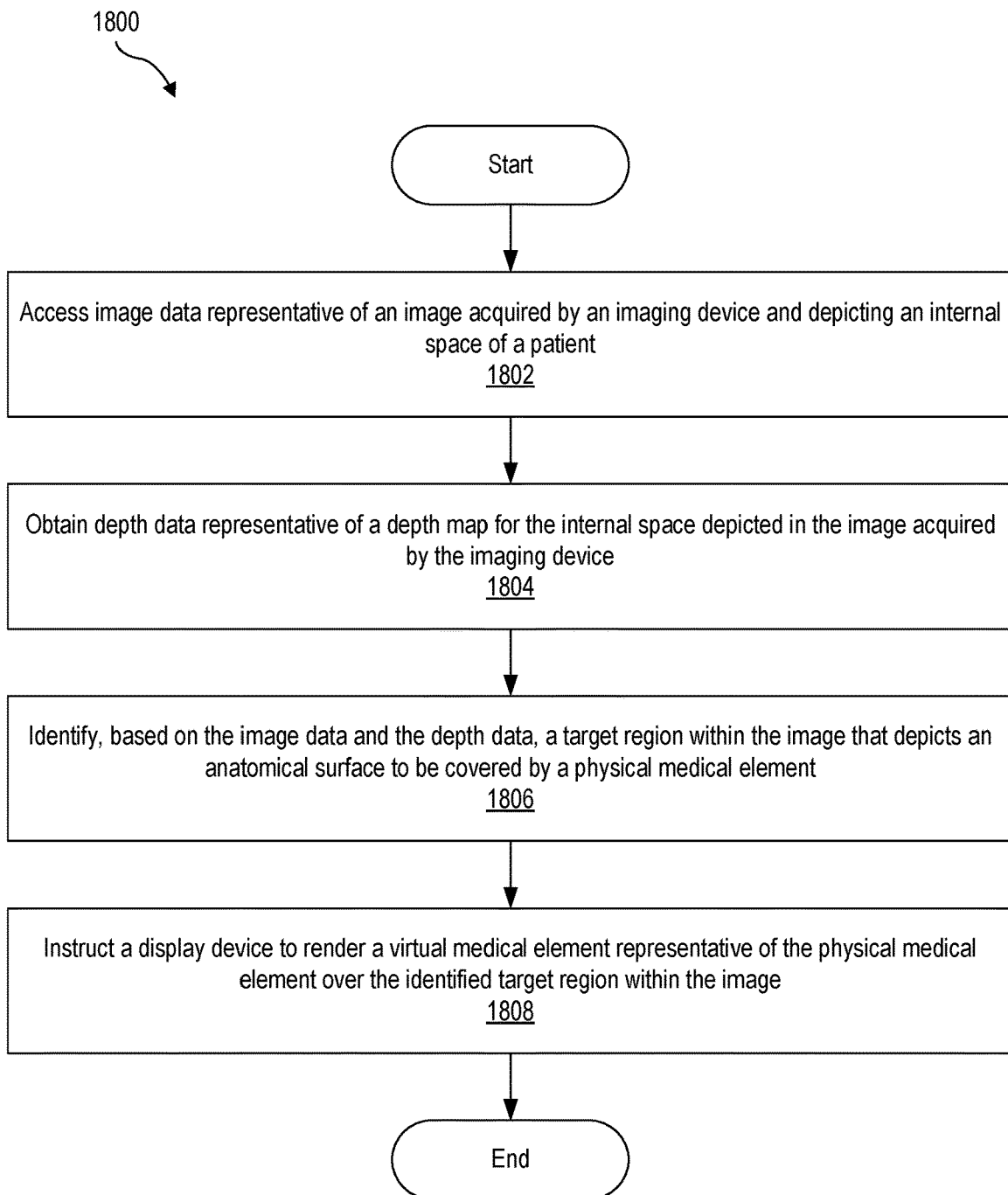

FIG. 18 illustrates another exemplary method 1800 that may be performed by a medical element management system (e.g., system 100 and/or any implementation thereof). While FIG. 18 illustrates exemplary operations according to one embodiment, other embodiments may omit, add to, reorder, and/or modify any of the operations shown in FIG. 18.

In operation 1802, a medical element management system accesses image data representative of an image acquired by an imaging device and depicting an internal space of a patient. Operation 1802 may be performed in any of the ways described herein.

In operation 1804, the medical element management system obtains depth data representative of a depth map for the internal space depicted in the image acquired by the imaging device. Operation 1804 may be performed in any of the ways described herein.

In operation 1806, the medical element management system identifies, based on the image data and the depth data, a target region within the image that depicts an anatomical surface to be covered by a physical medical element. Operation 1806 may be performed in any of the ways described herein.

In operation 1808, the medical element management system instructs a display device to render a virtual medical element representative of the physical medical element over the identified target region within the image. Operation 1808 may be performed in any of the ways described herein.

Figure 19:
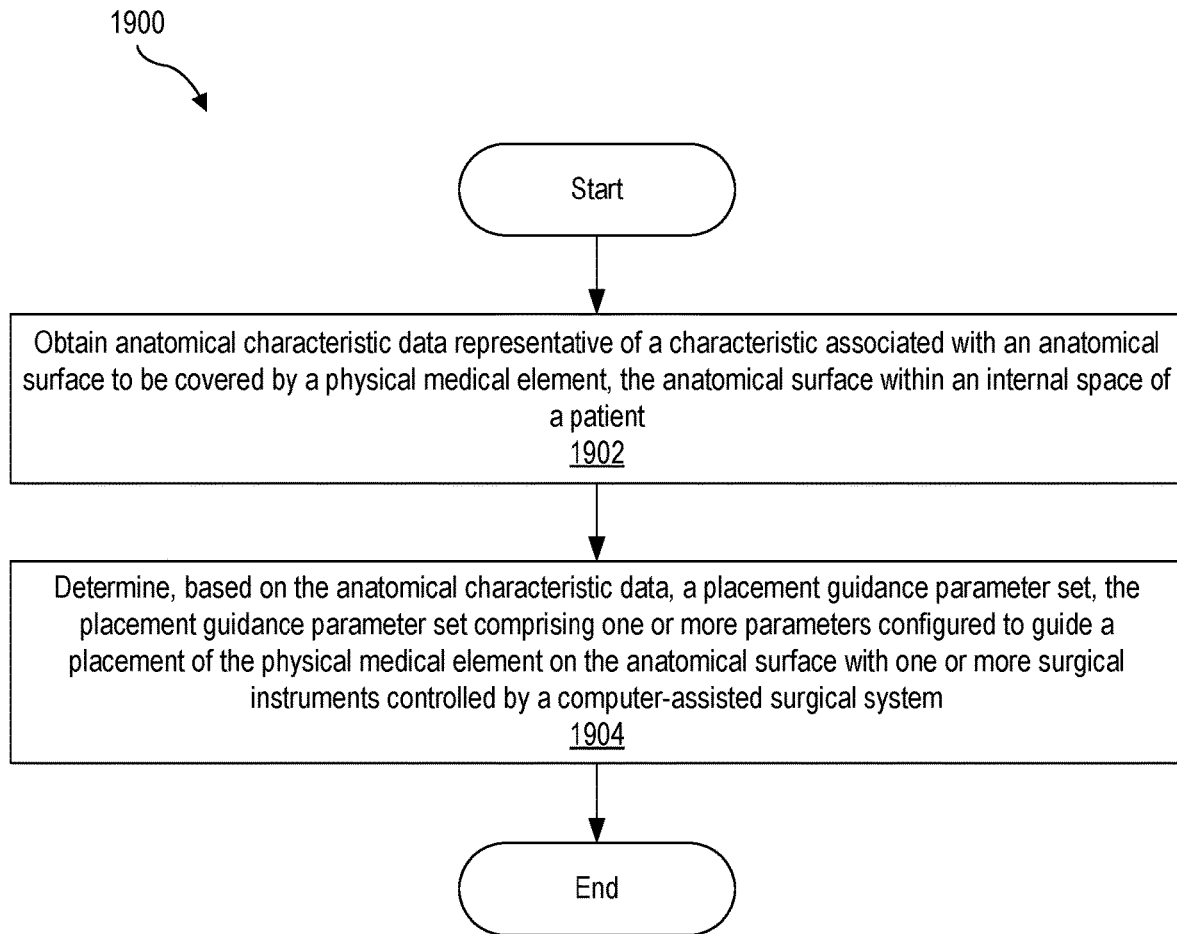

FIG. 19 illustrates another exemplary method 1900 that may be performed by a medical element management system (e.g., system 100 and/or any implementation thereof). While FIG. 19 illustrates exemplary operations according to one embodiment, other embodiments may omit, add to, reorder, and/or modify any of the operations shown in FIG. 19.

In operation 1902, a medical element management system obtains anatomical characteristic data representative of a characteristic associated with an anatomical surface to be covered by a physical medical element, the anatomical surface within an internal space of a patient. Operation 1902 may be performed in any of the ways described herein.

In operation 1904, the medical element management system determines, based on the anatomical characteristic data, a placement guidance parameter set, the placement guidance parameter set comprising one or more parameters configured to guide a placement of the physical medical element on the anatomical surface with one or more surgical instruments controlled by a computer-assisted surgical system. Operation 1904 may be performed in any of the ways described herein.

Figure 20:
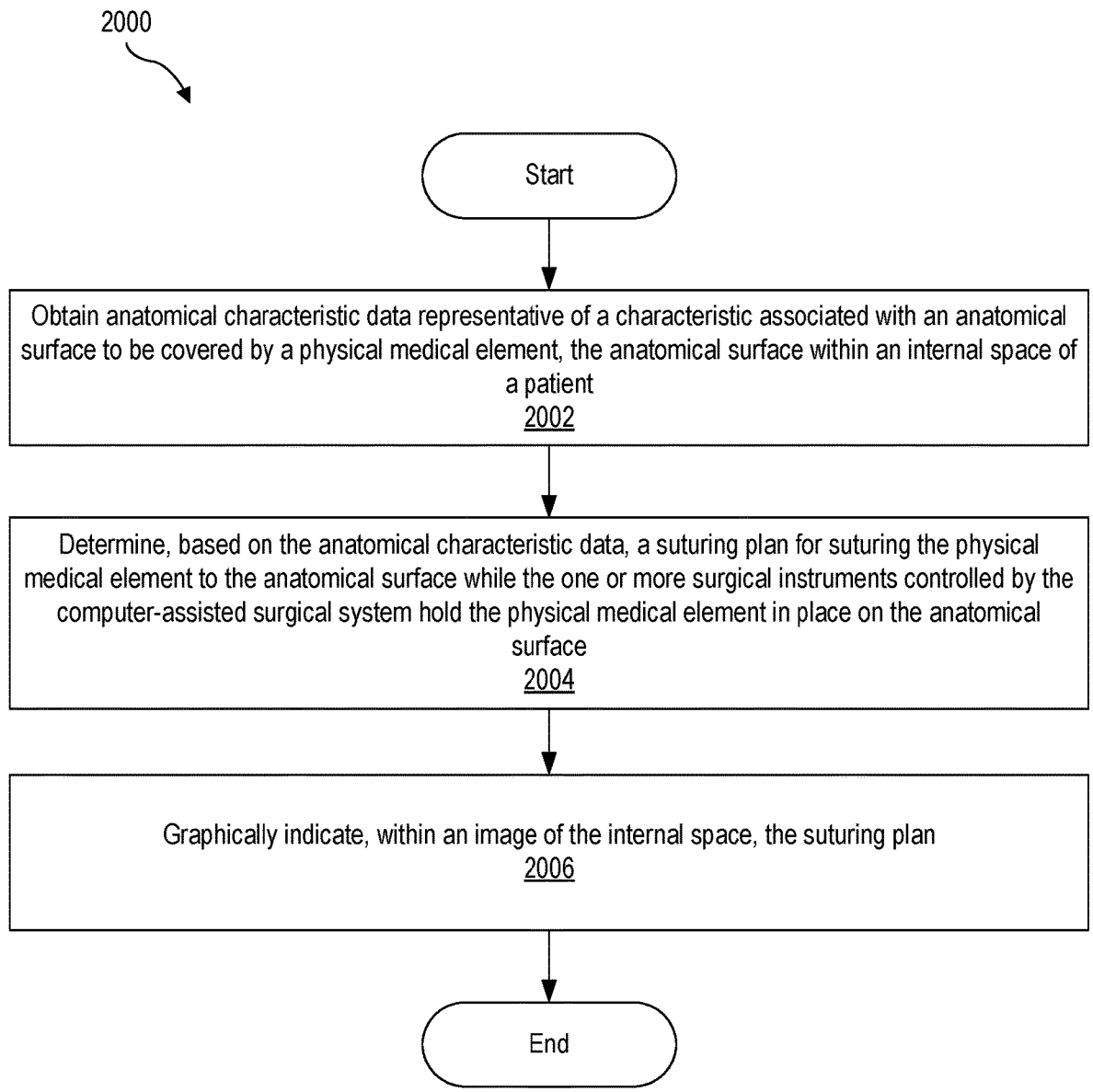

FIG. 20 illustrates another exemplary method 2000 that may be performed by a medical element management system (e.g., system 100 and/or any implementation thereof). While FIG. 20 illustrates exemplary operations according to one embodiment, other embodiments may omit, add to, reorder, and/or modify any of the operations shown in FIG. 20.

In operation 2002, a medical element management system obtains anatomical characteristic data representative of a characteristic associated with an anatomical surface to be covered by a physical medical element, the anatomical surface within an internal space of a patient. Operation 2002 may be performed in any of the ways described herein.

In operation 2004, the medical element management system determines, based on the anatomical characteristic data, a suturing plan for suturing the physical medical element to the anatomical surface while the one or more surgical instruments controlled by the computer-assisted surgical system hold the physical medical element in place on the anatomical surface. Operation 2004 may be performed in any of the ways described herein.

In operation 2006, the medical element management system graphically indicates, within an image of the internal space, the suturing plan. Operation 2006 may be performed in any of the ways described herein.

Figure 21:
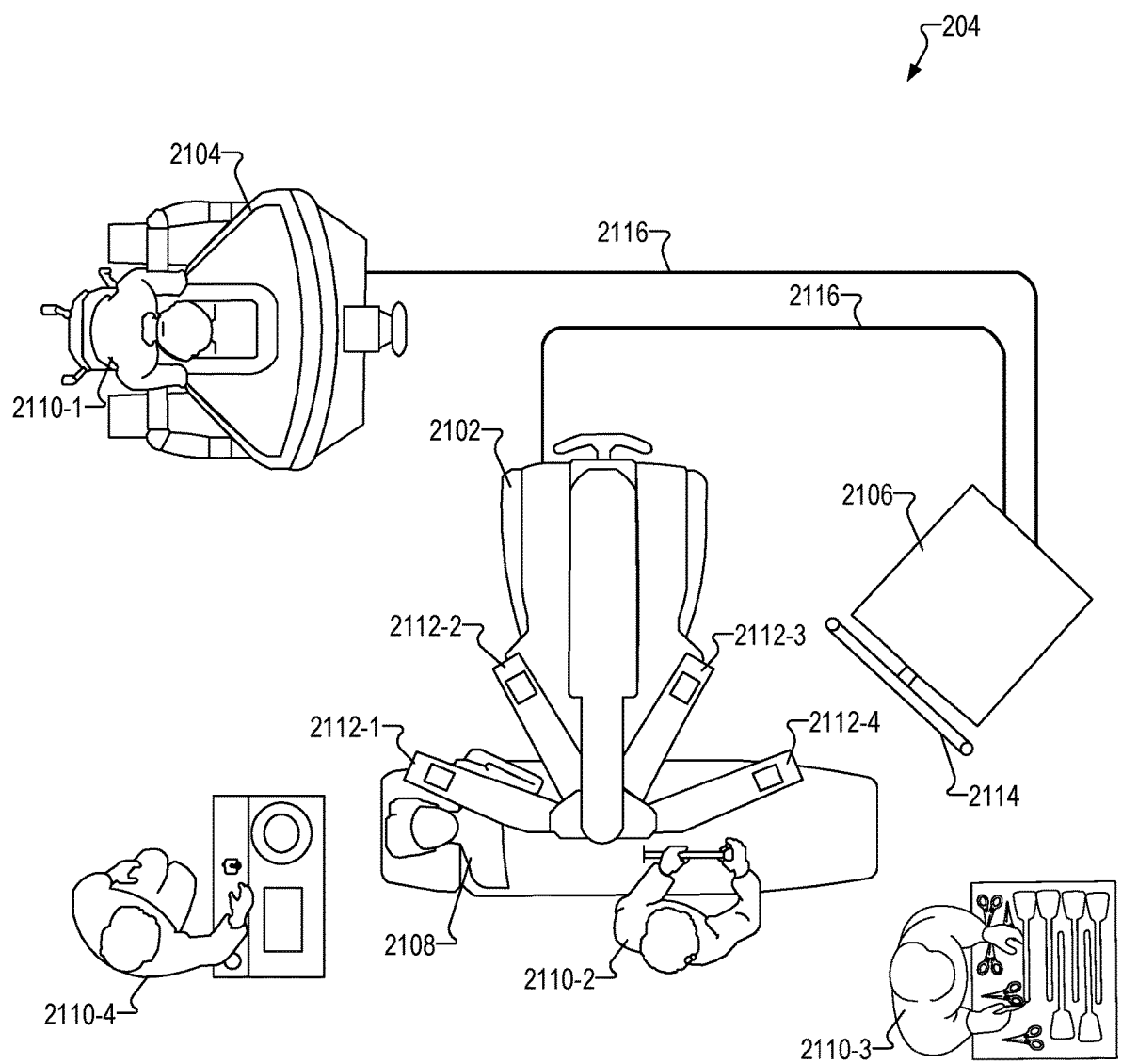
FIG. 21 illustrates an exemplary computer-assisted surgical system according to principles described herein.

The systems and methods described herein may be used in connection with and/or implemented by a computer-assisted surgical system used to perform a surgical procedure with respect to a patient. FIG. 21 illustrates an exemplary computer-assisted surgical system 2100 ("surgical system 2100"). As shown, surgical system 2100 may include a manipulating system 2102, a user control system 2104, and an auxiliary system 2106 communicatively coupled one to another. Surgical system 2100 may be utilized by a surgical team to perform a computer-assisted surgical procedure on a patient 2108. As shown, the surgical team may include a surgeon 2110-1, an assistant 2110-2, a nurse 2110-3, and an anesthesiologist 2110-4, all of whom may be collectively referred to as "surgical team members 2110." Additional or alternative surgical team members may be present during a surgical session as may serve a particular implementation.

While FIG. 21 illustrates an ongoing minimally invasive surgical procedure, it will be understood that surgical system 2100 may similarly be used to perform open surgical procedures or other types of surgical procedures that may similarly benefit from the accuracy and convenience of surgical system 2100. Additionally, it will be understood that the surgical session throughout which surgical system 2100 may be employed may not only include an operative phase of a surgical procedure, as is illustrated in FIG. 21, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 21, manipulating system 2102 may include a plurality of manipulator arms 2112 (e.g., manipulator arms 2112-1 through 2112-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 2108 (e.g., by being at least partially inserted into patient 2108 and manipulated to perform a computer-assisted surgical procedure on patient 2108). While manipulating system 2102 is depicted and described herein as including four manipulator arms 2112, it will be recognized that manipulating system 2102 may include only a single manipulator arm 2112 or any other number of manipulator arms as may serve a particular implementation.

Manipulator arms 2112 and/or surgical instruments attached to manipulator arms 2112 may include one or more displacement transducers, orientational sensors, and/or positional sensors used to generate raw (i.e., uncorrected) kinematics information. One or more components of surgical system 2100 may be configured to use the kinematics information to track (e.g., determine positions of) and/or control the surgical instruments.

User control system 2104 may be configured to facilitate control by surgeon 2110-1 of manipulator arms 2112 and surgical instruments attached to manipulator arms 2112. For example, surgeon 2110-1 may interact with user control system 2104 to remotely move or manipulate manipulator arms 2112 and the surgical instruments. To this end, user control system 2104 may provide surgeon 2110-1 with imagery (e.g., high-definition 3D imagery) of a surgical area associated with patient 2108 as captured by an imaging system (e.g., any of the medical imaging systems described herein). In certain examples, user control system 2104 may include a stereo viewer having two displays where stereoscopic images of a surgical area associated with patient 2108 and generated by a stereoscopic imaging system may be viewed by surgeon 2110-1. Surgeon 2110-1 may utilize the imagery to perform one or more procedures with one or more surgical instruments attached to manipulator arms 2112.

To facilitate control of surgical instruments, user control system 2104 may include a set of master controls. These master controls may be manipulated by surgeon 2110-1 to control movement of surgical instruments (e.g., by utilizing robotic and/or teleoperation technology). The master controls may be configured to detect a wide variety of hand, wrist, and finger movements by surgeon 2110-1. In this manner, surgeon 2110-1 may intuitively perform a procedure using one or more surgical instruments. In some examples, user control system 2104 implements user control system 806.

Auxiliary system 2106 may include one or more computing devices configured to perform primary processing operations of surgical system 2100. In such configurations, the one or more computing devices included in auxiliary system 2106 may control and/or coordinate operations performed by various other components (e.g., manipulating system 2102 and user control system 2104) of surgical system 2100. For example, a computing device included in user control system 2104 may transmit instructions to manipulating system 2102 by way of the one or more computing devices included in auxiliary system 2106. As another example, auxiliary system 2106 may receive, from manipulating system 2102, and process image data representative of imagery captured by an imaging device attached to one of manipulator arms 2112.

In some examples, auxiliary system 2106 may be configured to present visual content to surgical team members 2110 who may not have access to the images provided to surgeon 2110-1 at user control system 2104. To this end, auxiliary system 2106 may include a display monitor 2114 configured to display one or more user interfaces, such as images (e.g., 2D images, 3D images) of the surgical area, information associated with patient 2108 and/or the surgical procedure, and/or any other visual content as may serve a particular implementation. For example, display monitor 2114 may display images of the surgical area together with additional content (e.g., graphical content, contextual information, etc.) concurrently displayed with the images. In some embodiments, display monitor 2114 is implemented by a touchscreen display with which surgical team members 2110 may interact (e.g., by way of touch gestures) to provide user input to surgical system 2100.

Manipulating system 2102, user control system 2104, and auxiliary system 2106 may be communicatively coupled one to another in any suitable manner. For example, as shown in FIG. 21, manipulating system 2102, user control system 2104, and auxiliary system 2106 may be communicatively coupled by way of control lines 2116, which may represent any wired or wireless communication link as may serve a particular implementation. To this end, manipulating system 2102, user control system 2104, and auxiliary system 2106 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 22:
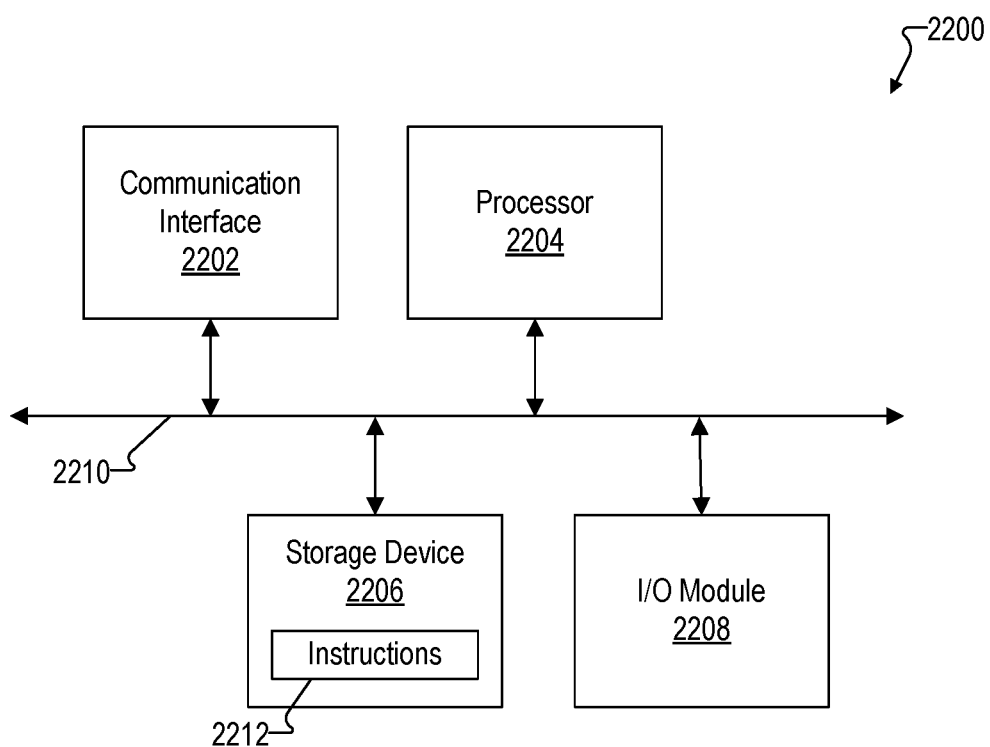
FIG. 22 illustrates an exemplary computing device according to principles described herein.

FIG. 22 illustrates an exemplary computing device 2200 that may be specifically configured to perform one or more of the processes described herein. Any of the systems, computing devices, and/or other components described herein may be implemented by computing device 2200.

As shown in FIG. 22, computing device 2200 may include a communication interface 2202, a processor 2204, a storage device 2206, and an input/output ("I/O") module 2208 communicatively connected one to another via a communication infrastructure 2210. While an exemplary computing device 2200 is shown in FIG. 22, the components illustrated in FIG. 22 are not intended to be limiting. Additional or alternative components may be used in other embodiments. Components of computing device 2200 shown in FIG. 22 will now be described in additional detail.

Communication interface 2202 may be configured to communicate with one or more computing devices. Examples of communication interface 2202 include, without limitation, a wired network interface (such as a network interface card), a wireless network interface (such as a wireless network interface card), a modem, an audio/video connection, and any other suitable interface.

Processor 2204 generally represents any type or form of processing unit capable of processing data and/or interpreting, executing, and/or directing execution of one or more of the instructions, processes, and/or operations described herein. Processor 2204 may perform operations by executing computer-executable instructions 2212 (e.g., an application, software, code, and/or other executable data instance) stored in storage device 2206.

Storage device 2206 may include one or more data storage media, devices, or configurations and may employ any type, form, and combination of data storage media and/or device. For example, storage device 2206 may include, but is not limited to, any combination of the non-volatile media and/or volatile media described herein. Electronic data, including data described herein, may be temporarily and/or permanently stored in storage device 2206. For example, data representative of computer-executable instructions 2212 configured to direct processor 2204 to perform any of the operations described herein may be stored within storage device 2206. In some examples, data may be arranged in one or more databases residing within storage device 2206.

I/O module 2208 may include one or more I/O modules configured to receive user input and provide user output. I/O module 2208 may include any hardware, firmware, software, or combination thereof supportive of input and output capabilities. For example, I/O module 2208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2208 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a non-transitory memory storing instructions; and
a processor communicatively coupled to the memory and configured to execute the instructions to:
access image data representative of an image acquired by an imaging device aimed at an internal space of a patient;
obtain depth data representative of a depth map for the internal space;
instruct a display device to render, based on the image data and the depth data, a virtual medical element over a target region within the image, the virtual medical element representative of a physical medical element that is to be introduced into the patient, the target region depicting an anatomical surface to be covered by the physical medical element when the physical medical element is introduced into the patient;
receive, while the virtual medical element is rendered over the target region, user input that sets at least one of a pose of the virtual medical element within the image or a size of the virtual medical element; and
determine, based on the user input and on the depth data, physical dimensions for sizing the physical medical element that is to be introduced into the patient.

2. The system of claim 1, wherein:
the processor is further configured to execute the instructions to access deformation data representative of a deformation model of the physical medical element; and
the determining of the physical dimensions for the physical medical element is further based on the deformation data.

3. The system of claim 1, wherein the determining of the physical dimensions of the physical medical element comprises:
identifying, based on the pose and the size of the virtual medical element, a plurality of pixels within the image that are covered by the virtual medical element;
determining a two-dimensional pixel area of the plurality of pixels;
determining, based on the depth data, depth values for each of the plurality of pixels;
determining, based on the two-dimensional pixel area and the depth values, a surface area of the anatomical surface to be covered by the physical medical element; and
basing the physical dimensions on the surface area of the anatomical surface.

4. The system of claim 3, wherein a surface area for the physical medical element as defined by the physical dimensions is greater than a physical area represented by the two-dimensional pixel area.

5. The system of claim 1, wherein the processor is further configured to execute the instructions to output data representative of the physical dimensions.

6. The system of claim 1, wherein the processor is further configured to execute the instructions to project the virtual medical element onto a physical material from which the physical medical element is to be cut.

7. The system of claim 1, wherein the receiving of the user input comprises receiving user input that adjusts at least one of the pose of the virtual medical element within the image or the size of the virtual medical element.

8. The system of claim 7, wherein the processor is further configured to execute the instructions to dynamically adjust, in response to receiving the user input that adjusts at least one of the pose of the virtual medical element within the image or the size of the virtual medical element, the rendering of the virtual medical element in substantially real time to depict at least one of the pose or the size of the virtual medical element as adjusted by the user input.

9. The system of claim 1, wherein:
the physical medical element comprises one or more of a mesh patch, gauze, a bandage, a plate, a prosthesis, a specimen containment bag, a fastener, or bone putty.

10. The system of claim 1, wherein the processor is further configured to execute the instructions to:
identify, based on the image data and the depth data, a region within the image that depicts tissue in need of being covered by the physical medical element; and
designate the region as the target region.

11. The system of claim 10, wherein the identifying of the region within the image that depicts tissue in need of being covered by the physical medical element comprises inputting the image data and the depth data into a machine learning model configured to identify a tissue anomaly.

12. The system of claim 10, wherein the identifying of the region within the image that depicts tissue in need of being covered by the physical medical element comprises:
segmenting, based on the image data and the depth data, the image; and
identifying the region based on the segmenting.

13. The system of claim 1, wherein the imaging device comprises a visible light camera and the image acquired by the imaging device comprises a two-dimensional visible light image acquired by the visible light camera.

14. The system of claim 13, wherein the obtaining of the depth data comprises directing a depth sensor in the imaging device and separate from the visible light camera to acquire the depth data while the imaging device is aimed at the internal space of the patient.

15. The system of claim 14, wherein the depth sensor comprises a time-of-flight sensor.

16. The system of claim 1, wherein the obtaining of the depth data comprises:
directing a first visible light camera included in the imaging device to acquire a first visible light image of the internal space;
directing a second visible light camera included in the imaging device to acquire a second visible light image of the internal space; and
generating, based on the first and second visible light images, the depth data.

17. The system of claim 1, wherein the obtaining of the depth data comprises accessing a preoperative image registered to the image.

18. The system of claim 17, wherein the preoperative image comprises an image generated by at least one of a computer-aided tomography (CT) scanner, a magnetic resonance imaging (MRI) device, an ultrasound device, or a three-dimensional scanning (LIDAR) device.

19. A method comprising:
accessing, by a medical element management system, image data representative of an image acquired by an imaging device aimed at an internal space of a patient;
obtaining, by the medical element management system, depth data representative of a depth map for the internal space;
instructing, by the medical element management system, a display device to render, based on the image data and the depth data, a virtual medical element over a target region within the image, the virtual medical element representative of a physical medical element that is to be introduced into the patient, the target region depicting an anatomical surface to be covered by the physical medical element when the physical medical element is introduced into the patient;
receiving, by the medical element management system while the virtual medical element is rendered over the target region, user input that sets at least one of a pose of the virtual medical element within the image or a size of the virtual medical element; and
determining, by the medical element management system based on the user input and on the depth data, physical dimensions for sizing the physical medical element that is to be introduced into the patient.

20. A non-transitory computer-readable medium storing instructions that, when executed, direct a processor of a computing device to:
access image data representative of an image acquired by an imaging device aimed at an internal space of a patient;
obtain depth data representative of a depth map for the internal space;
instruct a display device to render, based on the image data and the depth data, a virtual medical element over a target region within the image, the virtual medical element representative of a physical medical element that is to be introduced into the patient, the target region depicting an anatomical surface to be covered by the physical medical element when the physical medical element is introduced into the patient;

receive, while the virtual medical element is rendered over the target region, user input that sets at least one of a pose of the virtual medical element within the image or a size of the virtual medical element; and determine, based on the user input and on the depth data, physical dimensions for sizing the physical medical element that is to be introduced into the patient.

\* \* \* \* \*